United States Patent
Yokoyama et al.

(10) Patent No.: US 10,566,543 B2
(45) Date of Patent: Feb. 18, 2020

(54) PYRIMIDINE DERIVATIVE AND ORGANIC ELECTROLUMINESCENT DEVICES

(71) Applicant: HODOGAYA CHEMICAL CO., LTD., Tokyo (JP)

(72) Inventors: Norimasa Yokoyama, Tokyo (JP); Shuichi Hayashi, Tokyo (JP); Hideyoshi Kitahara, Tokyo (JP); Sung Keum Choi, Tokyo (JP); Si In Kim, Tokyo (JP); Ji Yung Kim, Tokyo (JP); Hyunju Oh, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 203 days.

(21) Appl. No.: 15/544,116

(22) PCT Filed: Jan. 13, 2016

(86) PCT No.: PCT/JP2016/050832
§ 371 (c)(1),
(2) Date: Jul. 17, 2017

(87) PCT Pub. No.: WO2016/117428
PCT Pub. Date: Jul. 28, 2016

(65) Prior Publication Data
US 2018/0006239 A1     Jan. 4, 2018

(30) Foreign Application Priority Data

Jan. 20, 2015  (JP) .................. 2015-008229

(51) Int. Cl.
*H01L 51/00* (2006.01)
*C07D 401/10* (2006.01)
(Continued)

(52) U.S. Cl.
CPC ........ *H01L 51/0067* (2013.01); *C07D 401/10* (2013.01); *C09K 11/06* (2013.01);
(Continued)

(58) Field of Classification Search
None
See application file for complete search history.

(56) References Cited

U.S. PATENT DOCUMENTS

| 5,869,199 A | 2/1999 | Kido |
| 2003/0165715 A1 | 9/2003 | Yoon et al. |

(Continued)

FOREIGN PATENT DOCUMENTS

| CN | 103396404 | 11/2013 |
| CN | 103951657 | 7/2014 |

(Continued)

OTHER PUBLICATIONS

European Search Report issued with respect to Application No. 16740036.5, dated May 24, 2018.
(Continued)

*Primary Examiner* — Robert S Loewe
(74) *Attorney, Agent, or Firm* — Greenblum & Bernstein, P.L.C.

(57) ABSTRACT

According to the present invention, there are provided pyrimidine derivatives represented by the following general formula (1). The pyrimidine derivatives of the invention are novel compounds and feature (1) good electron injection property, (2) high electron mobility, (3) excellent hole blocking property, (4) good stability in their form of thin films, and (5) excellent heat resistance.

(Continued)

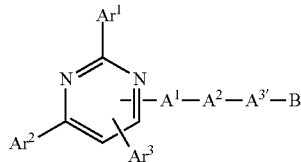

(1)

6 Claims, 25 Drawing Sheets

(51) Int. Cl.
 C09K 11/06  (2006.01)
 H01L 51/50  (2006.01)
 H01L 51/52  (2006.01)

(52) U.S. Cl.
 CPC ............ *H01L 51/50* (2013.01); *H01L 51/001* (2013.01); *H01L 51/5016* (2013.01); *H01L 51/5072* (2013.01); *H01L 51/5092* (2013.01); *H01L 51/5096* (2013.01); *H01L 51/5206* (2013.01); *H01L 51/5221* (2013.01)

(56) References Cited

U.S. PATENT DOCUMENTS

| | | | | |
|---|---|---|---|---|
| 2004/0086745 | A1* | 5/2004 | Iwakuma | C07D 401/10 428/690 |
| 2005/0127823 | A1* | 6/2005 | Iwakuma | C07D 401/04 313/504 |
| 2007/0190355 | A1 | 8/2007 | Ikeda et al. | |
| 2007/0257600 | A1 | 11/2007 | Matsuura et al. | |
| 2011/0156014 | A1* | 6/2011 | Kim | H01L 51/0067 257/40 |
| 2011/0291081 | A1* | 12/2011 | Inoue | C07D 401/14 257/40 |
| 2012/0104941 | A1* | 5/2012 | Jung | C07D 239/26 313/504 |
| 2012/0126208 | A1 | 5/2012 | Kawamura et al. | |
| 2012/0126690 | A1* | 5/2012 | Ise | C09K 11/06 313/504 |
| 2012/0126692 | A1 | 5/2012 | Ise et al. | |
| 2012/0214993 | A1* | 8/2012 | Aihara | C07D 239/26 544/180 |
| 2013/0032764 | A1* | 2/2013 | Buesing | C07D 239/26 252/500 |
| 2013/0079517 | A1 | 3/2013 | Schafer et al. | |
| 2014/0073784 | A1* | 3/2014 | Mizutani | C07D 405/14 544/216 |
| 2014/0084271 | A1* | 3/2014 | Lee | C07D 405/14 257/40 |
| 2014/0231769 | A1 | 8/2014 | Nishimura et al. | |
| 2014/0299192 | A1 | 10/2014 | Lee et al. | |
| 2014/0312338 | A1 | 10/2014 | Mizutani et al. | |
| 2015/0162543 | A1 | 6/2015 | Lee et al. | |
| 2016/0108072 | A1* | 4/2016 | Inoue | G02F 1/155 252/583 |
| 2016/0141514 | A1 | 5/2016 | Lee | |
| 2016/0172598 | A1* | 6/2016 | Lee | C07D 403/10 257/40 |
| 2016/0276600 | A1* | 9/2016 | Park | C07F 9/65128 |
| 2016/0380208 | A1* | 12/2016 | La | C07D 401/14 257/40 |

FOREIGN PATENT DOCUMENTS

| | | |
|---|---|---|
| EP | 2 461 390 | 6/2012 |
| JP | 2734341 | 1/1998 |
| JP | 2011-049512 | 3/2011 |
| JP | 2014-507383 | 3/2014 |
| KR | 10-2013-0060157 | 6/2013 |
| KR | 10-2014-0079306 | 6/2014 |
| WO | 03/060956 | 7/2003 |
| WO | 2004/039786 A1 | 5/2004 |
| WO | 2005/076669 | 8/2005 |
| WO | 2005/085387 | 9/2005 |
| WO | 2011/005060 | 1/2011 |
| WO | 2011/013783 | 2/2011 |
| WO | 2011/013830 | 2/2011 |
| WO | 2012/005360 | 1/2012 |
| WO | 2012/080052 | 6/2012 |
| WO | 2013/077362 | 5/2013 |
| WO | 2013/175746 | 11/2013 |
| WO | 2013/175747 | 11/2013 |
| WO | 2014/010824 | 1/2014 |
| WO | 2014/123238 A1 | 8/2014 |
| WO | 2014/208775 | 12/2014 |
| WO | 2014/208829 | 12/2014 |
| WO | 2014/209028 | 12/2014 |
| WO | WO-2014209028 | * 12/2014 ............ C07D 403/10 |

OTHER PUBLICATIONS

International Search Report issued in Patent Application No. PCT/JP2016/050832, dated Apr. 19, 2016.

* cited by examiner (COMPOUND 1)

(COMPOUND 2)

(COMPOUND 3)

(COMPOUND 4)

(COMPOUND 5)

(COMPOUND 6)

(COMPOUND 7)

(COMPOUND 8)

(COMPOUND 9)

(COMPOUND 10)

(COMPOUND 11)

(COMPOUND 12)

(COMPOUND 13)

(COMPOUND 14)

(COMPOUND 15)

(COMPOUND 16)

(COMPOUND 17)

(COMPOUND 18)

(COMPOUND 19)

(COMPOUND 20)

(COMPOUND 21)

(COMPOUND 22)

(COMPOUND 23)

(COMPOUND 24)

(COMPOUND 25)

(COMPOUND 26)

(COMPOUND 27)

(COMPOUND 28)

(COMPOUND 29)

(COMPOUND 30)

(COMPOUND 31)

(COMPOUND 32)

(COMPOUND 33)

(COMPOUND 34)

(COMPOUND 35)

(COMPOUND 36)

(COMPOUND 37)

(COMPOUND 38)

(COMPOUND 39)

(COMPOUND 40)

(COMPOUND 41)

(COMPOUND 42)

(COMPOUND 43)

(COMPOUND 44)

(COMPOUND 45)

(COMPOUND 46)

(COMPOUND 47)

(COMPOUND 48)

(COMPOUND 49)

(COMPOUND 50)

(COMPOUND 51)

(COMPOUND 52)

(COMPOUND 53)

(COMPOUND 54)

(COMPOUND 55)

(COMPOUND 56)

(COMPOUND 57)

(COMPOUND 58)

(COMPOUND 59)

(COMPOUND 60)

(COMPOUND 61)

(COMPOUND 62)

(COMPOUND 63)

(COMPOUND 64)

(COMPOUND 65)

(COMPOUND 66)

(COMPOUND 67)

(COMPOUND 68)

(COMPOUND 69)

(COMPOUND 70)

(COMPOUND 71)

(COMPOUND 72)

(COMPOUND 73)

(COMPOUND 74)

(COMPOUND 75)

(COMPOUND 76)

(COMPOUND 77)

(COMPOUND 78)

(COMPOUND 79)

(COMPOUND 80)

(COMPOUND 81)

(COMPOUND 82)

(COMPOUND 83)

(COMPOUND 84)

(COMPOUND 85)

(COMPOUND 86)

(COMPOUND 87)

(COMPOUND 88)

(COMPOUND 89)

(COMPOUND 90)

(COMPOUND 91)

(COMPOUND 92)

(COMPOUND 93)

(COMPOUND 94)

(COMPOUND 95)

(COMPOUND 96)

(COMPOUND 97)

(COMPOUND 98)

(COMPOUND 99)

(COMPOUND 100)

(COMPOUND 101)

(COMPOUND 102)

(COMPOUND 103)

(COMPOUND 104)

(COMPOUND 105)

(COMPOUND 106)

(COMPOUND 107)

(COMPOUND 108)

(COMPOUND 109)

(COMPOUND 110)

(COMPOUND 111)

(COMPOUND 112)

(COMPOUND 113)

9: CATHODE
8: ELECTRON INJECTION LAYER
7: ELECTRON-TRANSPORTING LAYER
6: HOLE-BLOCKING LAYER
5: LUMINOUS LAYER
4: HOLE-TRANSPORTING LAYER
3: HOLE INJECTION LAYER
2: TRANSPARENT ANODE
1: GLASS SUBSTRATE

PYRIMIDINE DERIVATIVE AND ORGANIC ELECTROLUMINESCENT DEVICES

TECHNICAL FIELD

This invention relates to compounds adapted to producing organic electroluminescent devices and to organic electroluminescent devices (hereinafter often called organic EL devices). More specifically, the invention relates to pyrimidine derivatives and to organic EL devices using the pyrimidine derivatives.

BACKGROUND ART

Organic EL devices are self light-emitting devices which feature higher brightness and higher legibility than those of liquid crystal devices enabling vivid display to be realized, and have, therefore, been vigorously studied.

In 1987, C. W. Tang et al. of Eastman Kodak Company have developed a device of a laminated structure comprising various kinds of materials to bear individual roles, and have put an organic EL device using organic materials into a practical use. The above organic EL device is constituted by laminating layers of a fluorescent body capable of transporting electrons and of an organic material capable of transporting holes. Because of this configuration, the organic EL device is adapted to inject positive charges and negative charges into the layer of the fluorescent body to perform light emission, thereby obtaining a high luminance of 1,000 $cd/m^2$ or more at a voltage of 10V or less.

So far, many improvements have been made to put the organic EL device into practical use. For example, it is generally well known that high efficiency and durability can be achieved by an electroluminescence device having a laminated structure, in which the roles to be played by respective layers are further segmented, i.e., having an anode, a hole injection layer, a hole transport layer, a luminous layer, an electron transport layer, an electron injection layer, and a cathode on a substrate.

To further improve the luminous efficiency, attempts have been made to utilize triplet excitons and study has been forwarded to utilize a phosphorescent luminous compound. Devices have, further, been developed utilizing the emission of light based on the thermally activated delayed fluorescence (TADF). In 2011, Adachi et al. of Kyushu University has realized an external quantum efficiency of 5.3% by using a device comprising a thermally activated delayed fluorescent material.

The luminous layer is, usually, prepared by doping a charge transporting compound called host material with a fluorescent compound, a phosphorescent luminous compound or a material that emits delayed fluorescence. Selection of the organic materials in the organic EL device seriously affects the properties of the device, such as efficiency and durability.

In the organic EL device, the charges injected from both electrodes recombine together in the luminous layer to emit light. In the organic EL device, therefore, what is important is how efficiently to pass the charges of holes and electrons over to the luminous layer. Upon improving the electron injection property, improving the mobility thereof and, therefore, improving the probability of recombination of the holes and the electrons and, further, confining the excitons formed in the luminous layer, it is allowed to attain a high luminous efficiency. Namely, the electron transporting material plays an important role. Therefore, it has been desired to provide an electron transporting material that has a high electron injection property, a high electron mobility, a high hole blocking property and a large durability against the holes.

As for the device life, further, the heat resistance and amorphousness of the material also serve as important factors. The material having low heat resistance is subject to be thermally decomposed even at a low temperature due to the heat generated when the device is driven, and is deteriorated. The material having low amorphousness permits the thin film thereof to be crystallized even in short periods of time and, therefore, the device to be deteriorated. Therefore, the material to be used must have high heat resistance and good amorphousness.

Tris(8-hydroxyquinoline) aluminum (Alq) which is a representative luminous material has also been generally used as an electron transporting material having, however, a hole blocking property which is far from satisfactory.

A method of inserting a hole blocking layer is one of the measures for preventing the holes from partly passing through the luminous layer to improve the probability of recombination of the charges in the luminous layer. As a hole blocking material used for forming the hole blocking layer, there have heretofore been known triazole derivatives (see, for example, a patent document 1), a bathocuproin (BCP), a mixed ligand complex of aluminum [aluminum (III) bis(2-methyl-8-quinolinato)-4-phenyl phenolate (BAlq) and the like.

There has, further, been known a 3-(4-biphenylyl)-4-phenyl-5-(4-t-butylphenyl)-1,2,4-triazole (TAZ) as an electron transporting material having excellent hole blocking property (see a patent document 2). The TAZ has a work function of as large as 6.6 eV and a large hole blocking power. Therefore, the TAZ is used as a hole blocking material having an electron transport property, is laminated on the cathode side of a fluorescent luminous layer or a phosphorescent luminous layer prepared by vacuum evaporation or by coating, and is contributing to improving the efficiency of the organic EL devices. Because of its serious problem of low electron transport property, however, the TAZ had to be used in combination with an electron transporting material having a higher electron transport property.

The BCP, on the other hand, has a work function of as large as 6.7 eV and a large hole blocking power but a glass transition temperature (Tg) of as low as 83° C. In the form of a thin film, therefore, the BCP lacks stability and still cannot be said to be sufficiently working as the hole blocking layer.

As described above, either material still lacks stability when it is formed into a film or lacks the function for blocking the holes to a sufficient degree. In order to improve characteristics of the organic EL devices, therefore, it has been desired to provide an organic compound that excels in electron injection/transport performance and in hole blocking power, and features high stability in the form of a thin film.

PRIOR ART DOCUMENTS

Patent Documents

Patent document 1: Japanese Patent No. 2734341
Patent document 2: International Laid-Open WO2003/060956

OUTLINE OF THE INVENTION

Problems that the Invention is to Solve

The object of the present invention is to provide an organic compound that has excellent property, i.e., excels in electron injection/transport performance, features a hole blocking power and a high stability in the form of a thin film, and can be used as a material for producing organic EL devices.

Another object of the present invention is to provide an organic EL device which features a high efficiency, a low driving voltage and a large durability by using the above compound.

Means for Solving the Problems

To achieve the above object, the present inventors have paid attention to that a pyrimidine ring has affinity to electron, that a nitrogen atom of a pyrimidine ring is capable of being coordinated on a metal, and that the pyrimidine ring has excellent heat resistance. The inventors, further, have designed and chemically synthesized a compound that has the pyrimidine ring structure, have prepared various organic EL devices by using the above compound on an experimental basis, and have keenly evaluated the properties of the device. As a result, the inventors have completed the present invention.

Namely, according to the present invention, there are provided pyrimidine derivatives represented by the following general formula (1),

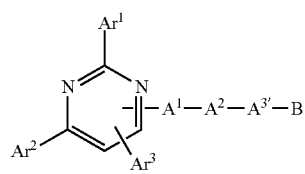

(1)

wherein,
Ar$^1$ and Ar$^2$ are, respectively, aromatic hydrocarbon groups or condensed polycyclic aromatic groups,
Ar$^3$ is a hydrogen atom, an aromatic hydrocarbon group or a condensed polycyclic aromatic group,
A$^1$ and A$^2$ are, respectively, divalent aromatic hydrocarbon groups or divalent condensed polycyclic aromatic groups,
A$^3$ is a divalent aromatic hydrocarbon group, a divalent condensed polycyclic aromatic group, or a single bond, and
B is an aromatic heterocyclic group.

In the pyrimidine derivatives of the present invention, it is desired that:
1) The pyrimidine derivatives are presented by the following general formula (1-1)

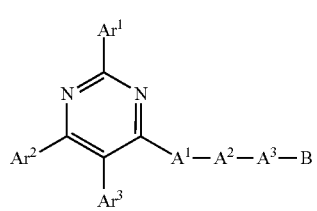

(1-1)

wherein,
Ar$^1$ to Ar$^3$, A$^1$ to A$^3$ and B are as defined in the above general formula (1);

2) The pyrimidine derivatives are represented by the following general formula (1-2),

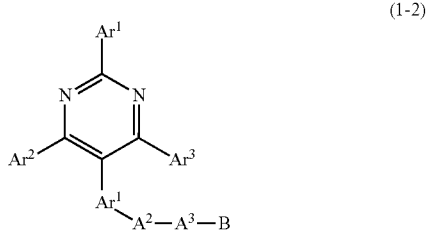

(1-2)

wherein,
Ar$^1$ to Ar$^3$, A$^1$ to A$^3$ and B are as defined in the above general formula (1);
3) A$^1$ or A$^2$ is a phenylene group;
4) A$^1$ and A$^2$ are phenylene groups;
5) A$^1$ or A$^2$ is a naphthylene group;
6) B is pyridyl group, bipyridyl group, terpyridyl group, pyrimidinyl group, pyradinyl group, triadinyl group, pyrolyl group, pyrazolyl group, imidazolyl group, furyl group, thienyl group, quinolyl group, isoquinolyl group, quinoxalynyl group, quinazolynyl group, naphthyridinyl group, indolyl group, benzoimidazolyl group, benzotriazolyl group, benzofuranyl group, benzothienyl group, benzoxazolyl group, benzothiazolyl group, benzothiadiazolyl group, pyridopyrolyl group, pyridoimidazolyl group, pyridotriazolyl group, acrydinyl group, phenadinyl group, phenanthrolynyl group, phenoxadinyl group, phenothiadinyl group, carbazolyl group, carbolynyl group, dibenzofuranyl group or dibenzothienyl group;
7) Ar$^2$ is a phenyl group;
8) Ar$^2$ is a condensed polycyclic aromatic group and, specifically, a naphthyl group or a phenanthrenyl group;
9) Ar$^3$ is a hydrogen atom;
10) Ar$^1$ is a phenyl group that has a substituent, the substituent possessed by the phenyl group being a condensed polycyclic aromatic group that has no substituent; and
11) Ar$^1$ is a condensed polycyclic aromatic group and, specifically, a condensed polycyclic aromatic group having no substituent.

According to the present invention, further, there is provided an organic EL device having a pair of electrodes and at least one organic layer held therebetween, the at least one organic layer containing the pyrimidine derivative.

In the organic EL device of the invention, it is desired that the organic layer containing the pyrimidine derivative is the electron transport layer, the hole blocking layer, the luminous layer or the electron injection layer.

Effects of the Invention

The pyrimidine derivatives of the invention are novel compounds and feature (1) good electron injection property, (2) high electron mobility, (3) excellent hole blocking power, (4) good stability in the form of its thin film, and (5) excellent heat resistance. Specifically, as demonstrated in Examples appearing later, the pyrimidine derivatives of the invention exhibit a work function which is greater by about 1 than the work function of 5.5 eV exhibited by the conventional hole transporting materials and, therefore, have a very high hole blocking power.

As compared to the conventional materials, the pyrimidine derivatives of the invention have favorable electron injection property and feature a high electron mobility. Therefore, if the pyrimidine derivatives of the invention are used as materials for constituting the electron injection layer and/or the electron transport layer of the organic EL device, the electrons are transported highly efficiently from the electron transport layer into the luminous layer contributing to improving the luminous efficiency and, at the same time, lowering the driving voltage and improving durability of the organic EL device.

The pyrimidine derivatives of the present invention have excellent hole blocking power as well as superior electron transport property to that of the conventional materials and, besides, remain highly stable in their form of a thin film. By using the pyrimidine derivatives of the invention as materials for constituting the hole blocking layer of the organic EL device, therefore, the organic EL device is driven on a decreased voltage, and exhibits an improved resistance against the electric current and an improved maximum brightness yet maintaining a high luminous efficiency.

The pyrimidine derivatives of the invention have a higher electron transport property and a wider band gap than those of the conventional materials, and can be used as materials for constituting the luminous layer of the organic EL device. Specifically, when being used as a host material of the luminous layer, the pyrimidine derivatives of the invention are capable of carrying a fluorescent luminous body or a phosphorescent luminous body called dopant. Therefore, there can be realized an organic EL device that drives on a decreased voltage and features an improved luminous efficiency.

The organic EL device of the present invention uses the pyrimidine derivative that has a higher electron injection power, a larger mobility, a larger hole blocking property, a higher stability against the holes and a higher stability in the form of thin film than those of the conventional electron transporting materials. Therefore, the organic EL device is capable of confining the excitons formed in the luminous layer, improving the probability of recombination of the holes with the electrons, attaining a high luminous efficiency and a high power efficiency, as a result, lowering the luminance start voltage and the practicable driving voltage, and realizing an elongated device life.

MODES FOR CARRYING OUT THE INVENTION

Figure 1:
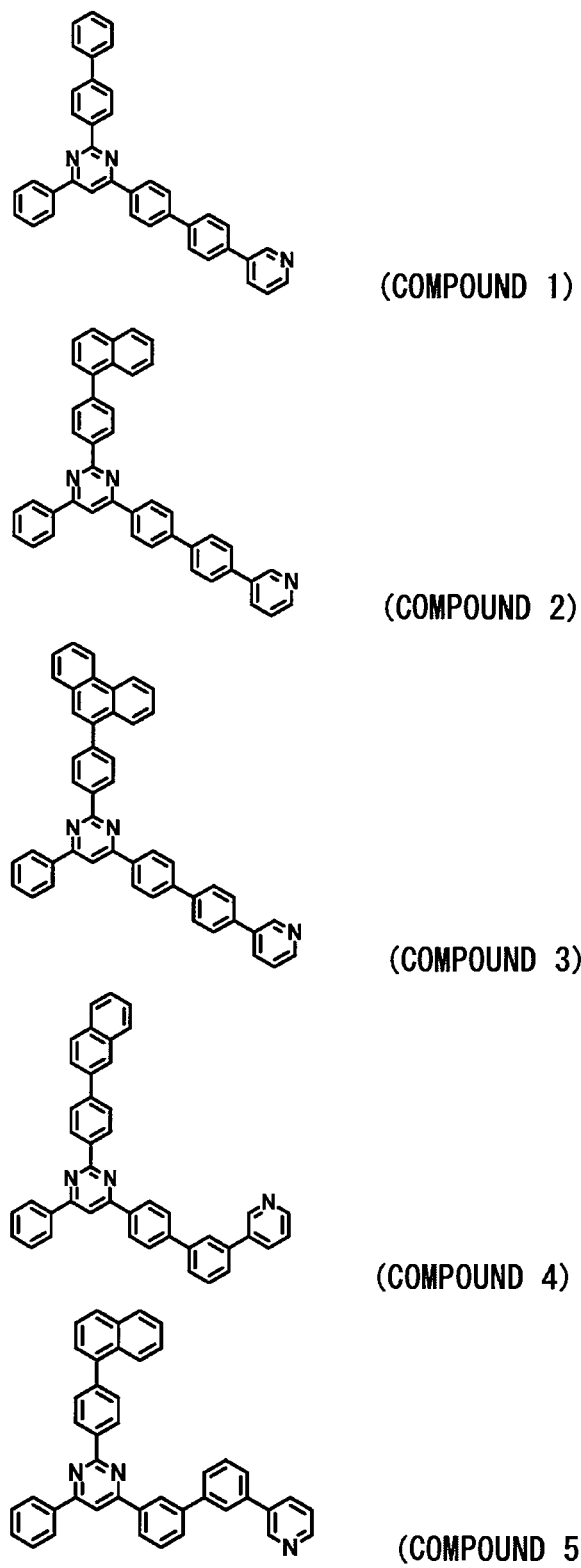
FIG. 1 A diagram showing a compound 1 to a compound 5 which are pyrimidine derivatives of the present invention.
Figure 2:
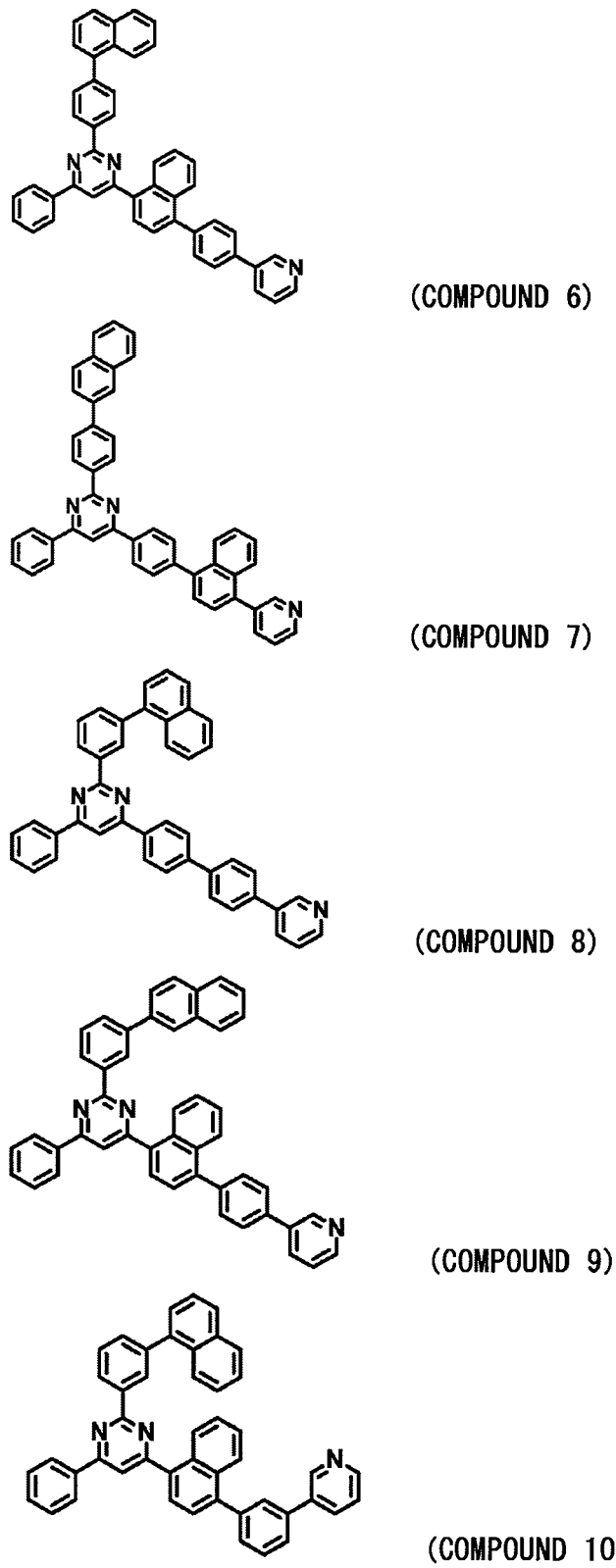
FIG. 2 A diagram showing a compound 6 to a compound 10 which are pyrimidine derivatives of the present invention.
Figure 3:
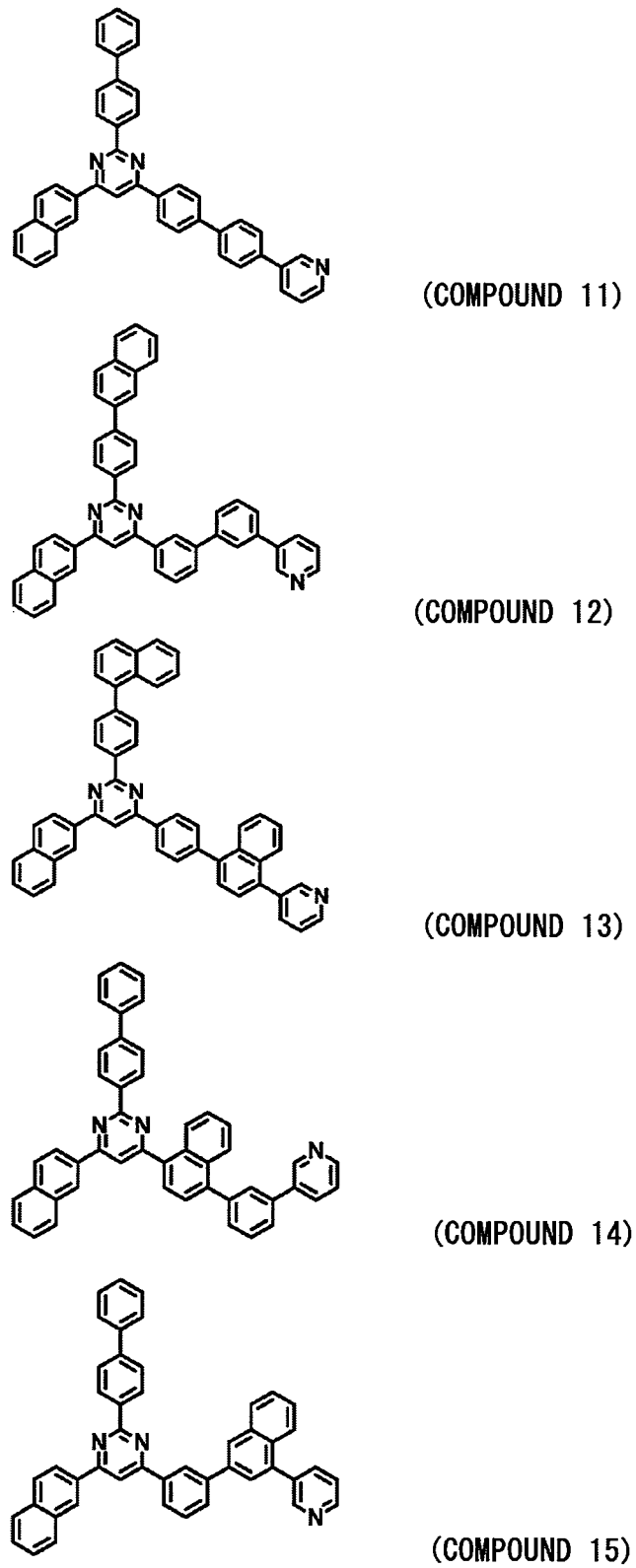
FIG. 3 A diagram showing a compound 11 to a compound 15 which are pyrimidine derivatives of the present invention.
Figure 4:
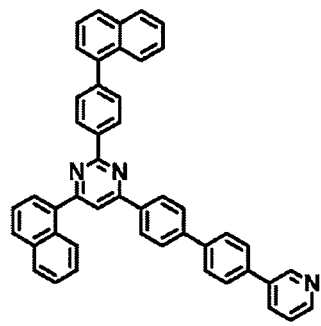
FIG. 4 A diagram showing a compound 16 to a compound 20 which are pyrimidine derivatives of the present invention.
Figure 4:
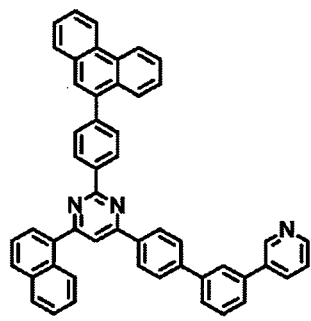
Figure 4:
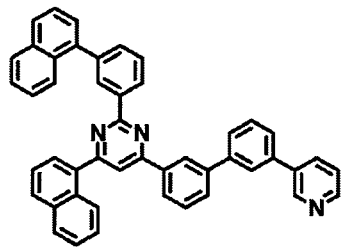
Figure 4:
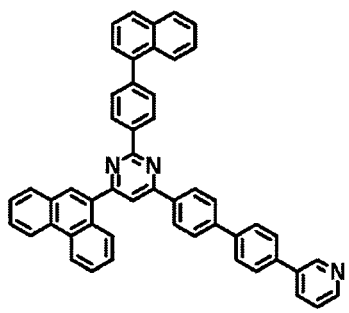
Figure 4:
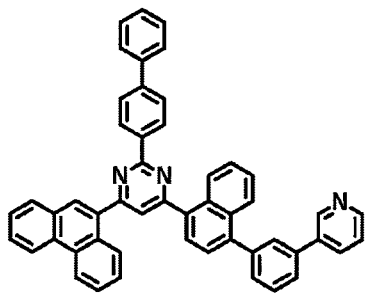
Figure 5:
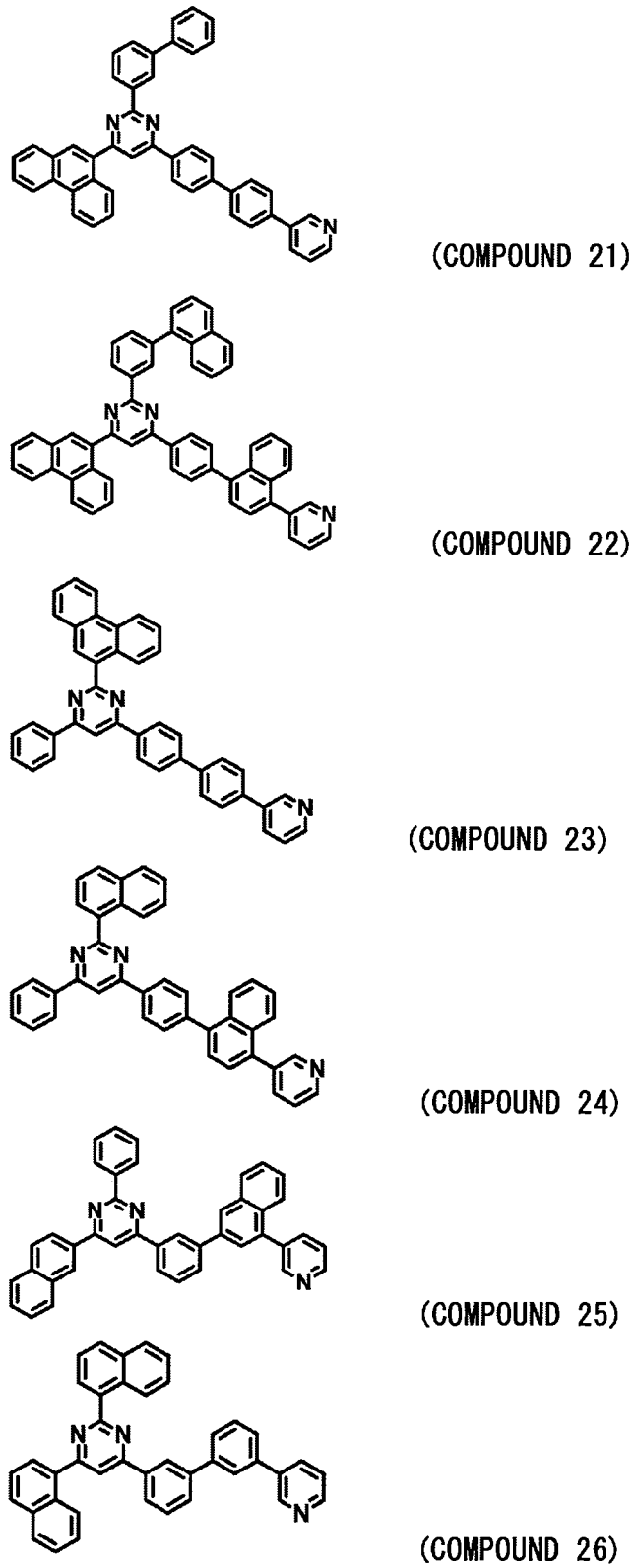
FIG. 5 A diagram showing a compound 21 to a compound 26 which are pyrimidine derivatives of the present invention.
Figure 6:
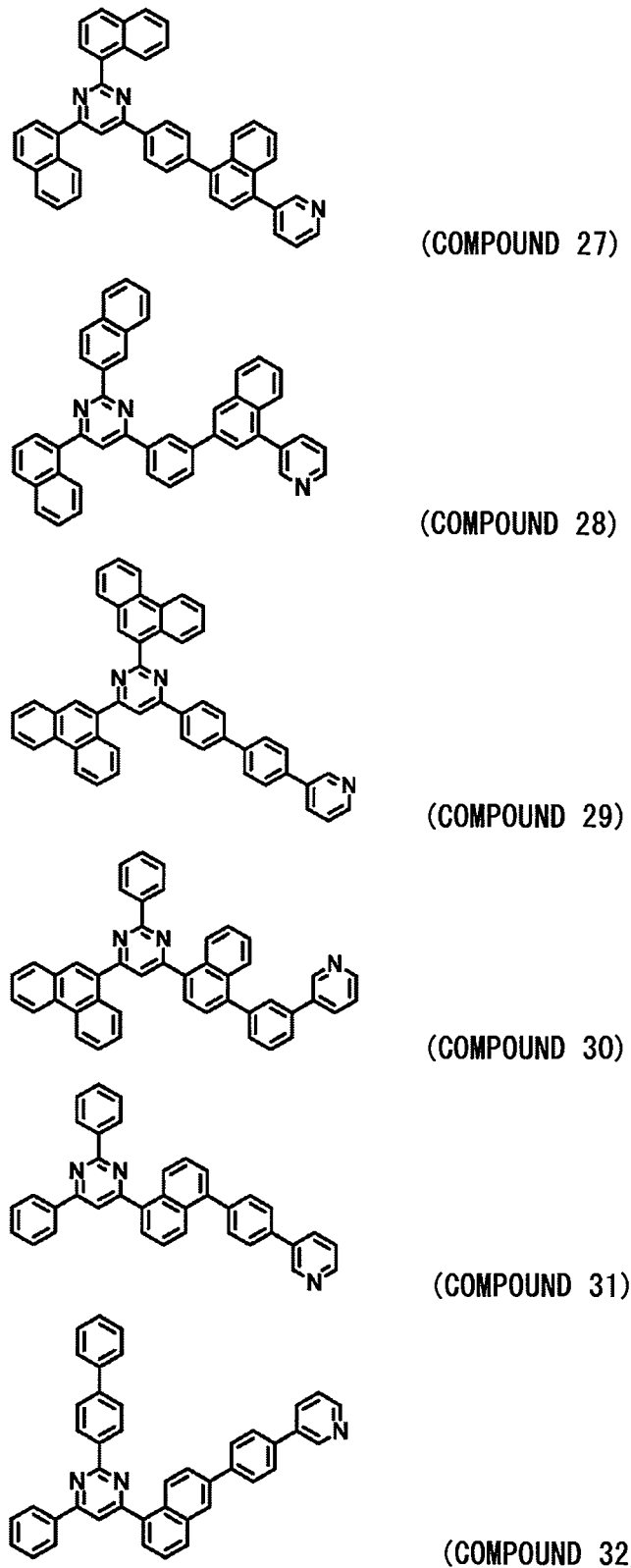
FIG. 6 A diagram showing a compound 27 to a compound 32 which are pyrimidine derivatives of the present invention.
Figure 7:
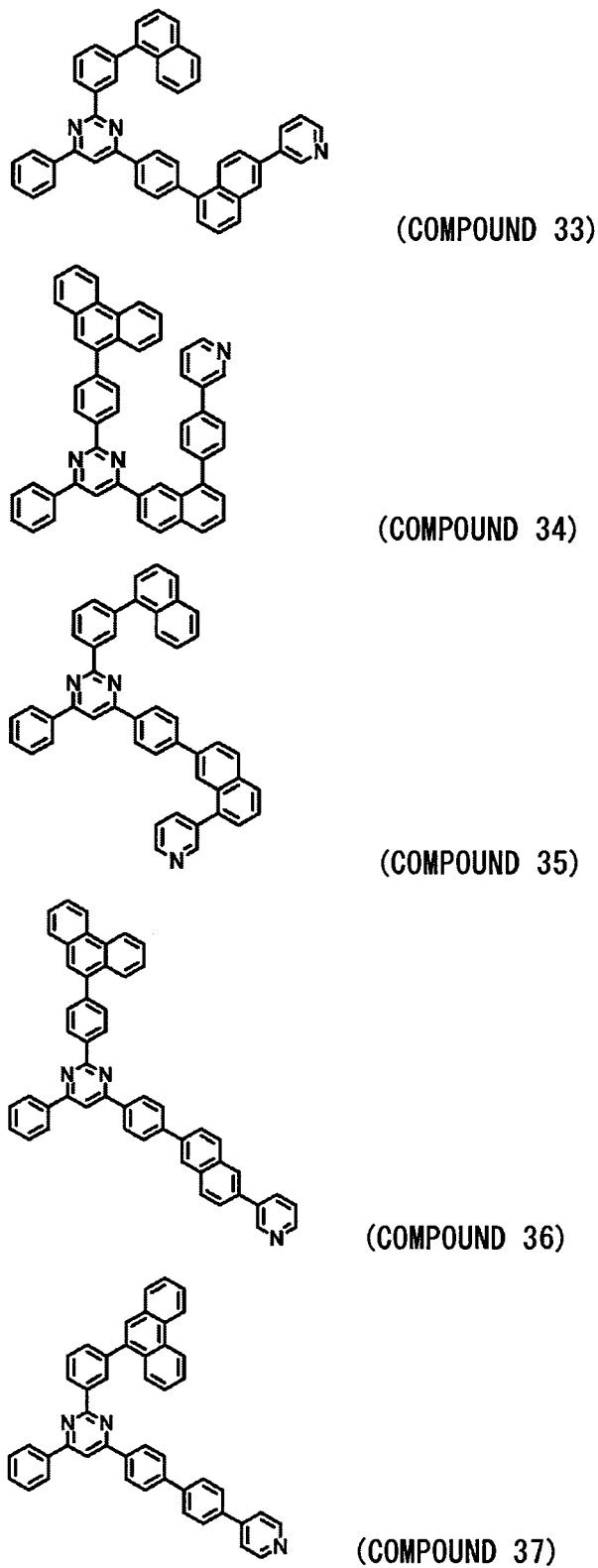
FIG. 7 A diagram showing a compound 33 to a compound 37 which are pyrimidine derivatives of the present invention.
Figure 8:
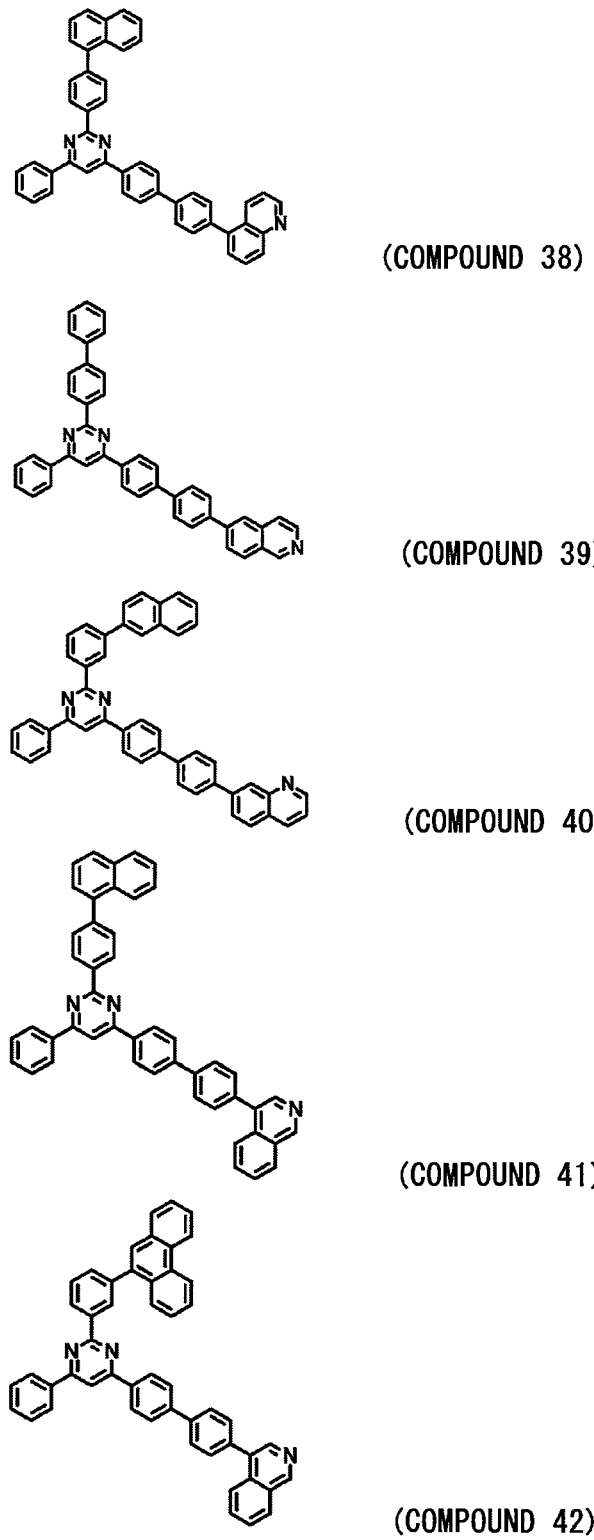
FIG. 8 A diagram showing a compound 38 to a compound 42 which are pyrimidine derivatives of the present invention.
Figure 9:
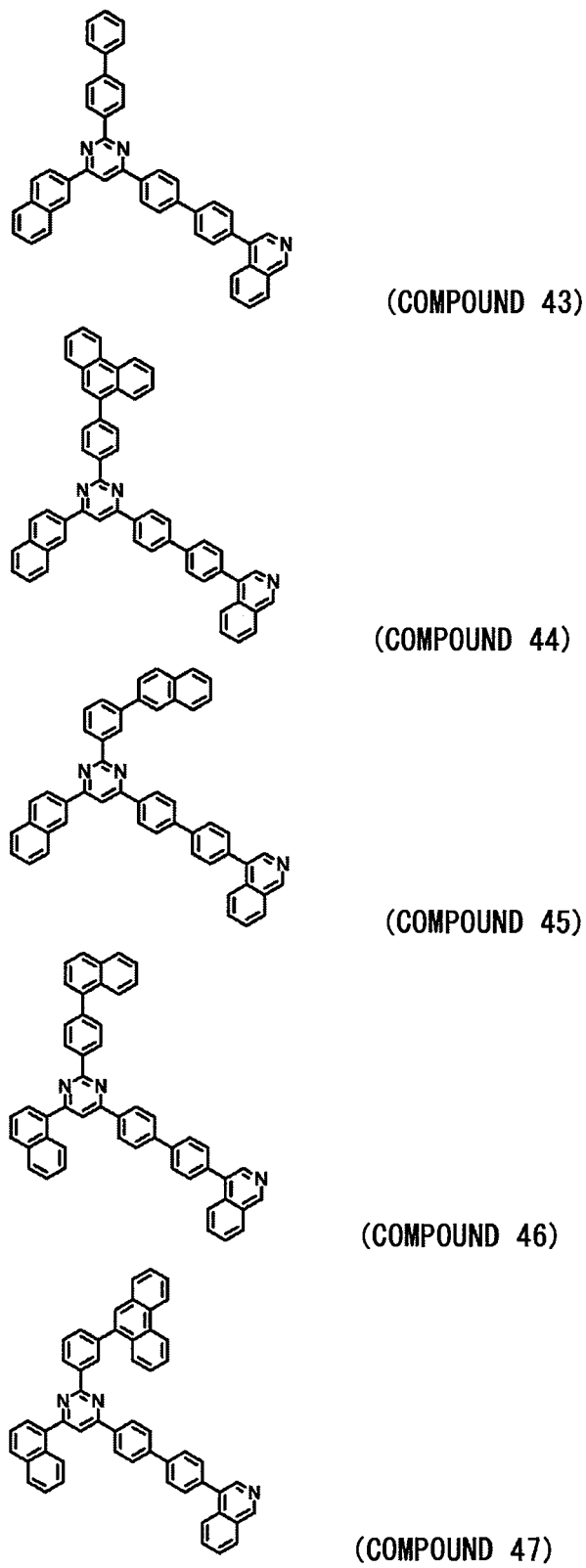
FIG. 9 A diagram showing a compound 43 to a compound 47 which are pyrimidine derivatives of the present invention.
Figure 10:
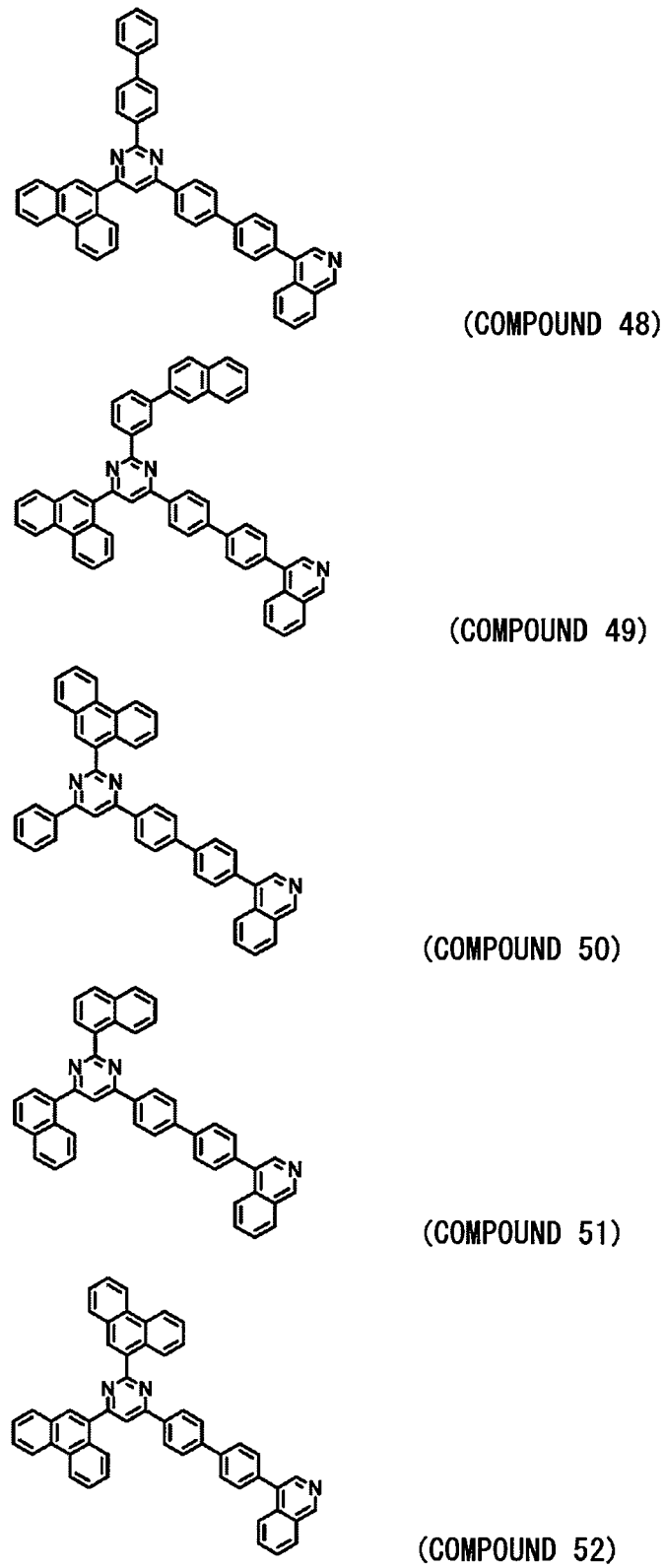
FIG. 10 A diagram showing a compound 48 to a compound 52 which are pyrimidine derivatives of the present invention.
Figure 11:
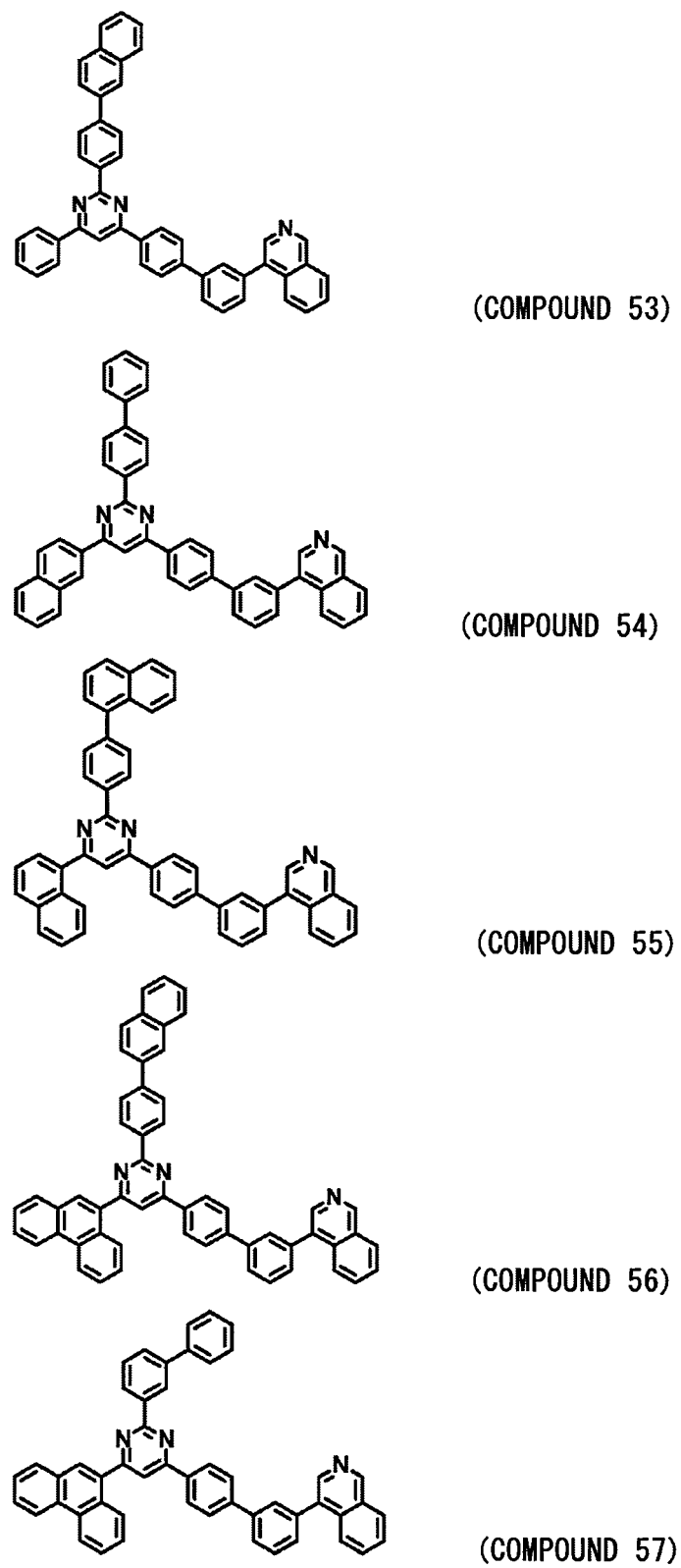
FIG. 11 A diagram showing a compound 53 to a compound 57 which are pyrimidine derivatives of the present invention.
Figure 12:
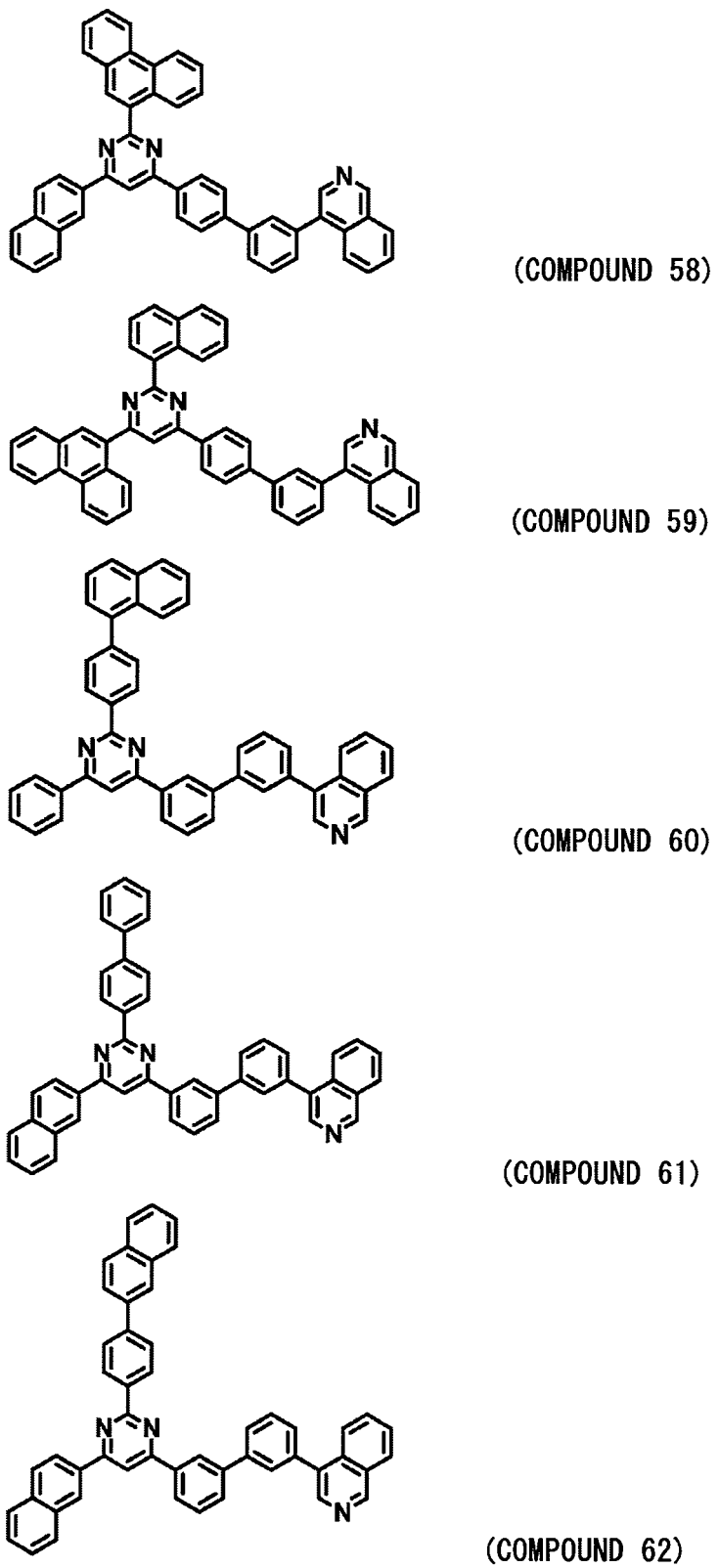
FIG. 12 A diagram showing a compound 58 to a compound 62 which are pyrimidine derivatives of the present invention.
Figure 13:
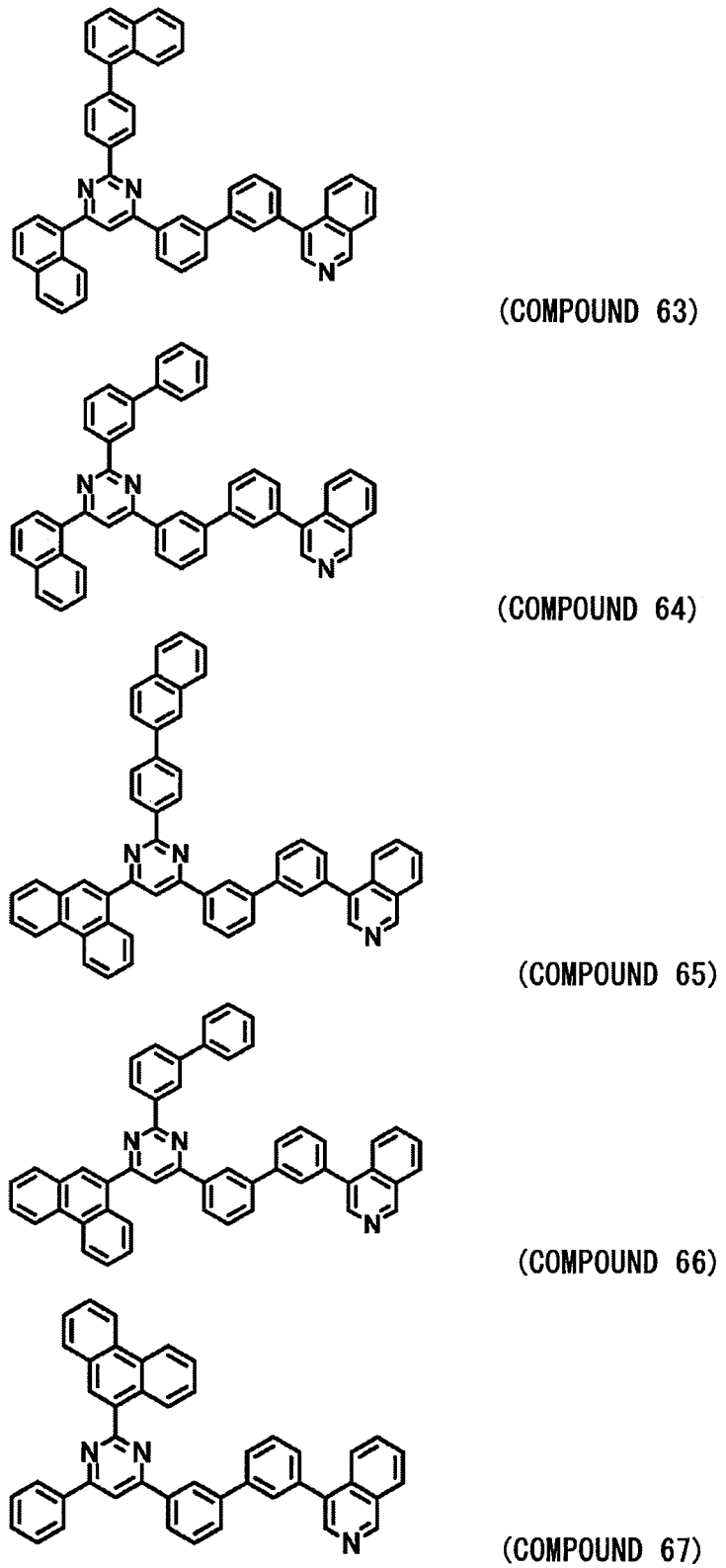
FIG. 13 A diagram showing a compound 63 to a compound 67 which are pyrimidine derivatives of the present invention.
Figure 14:
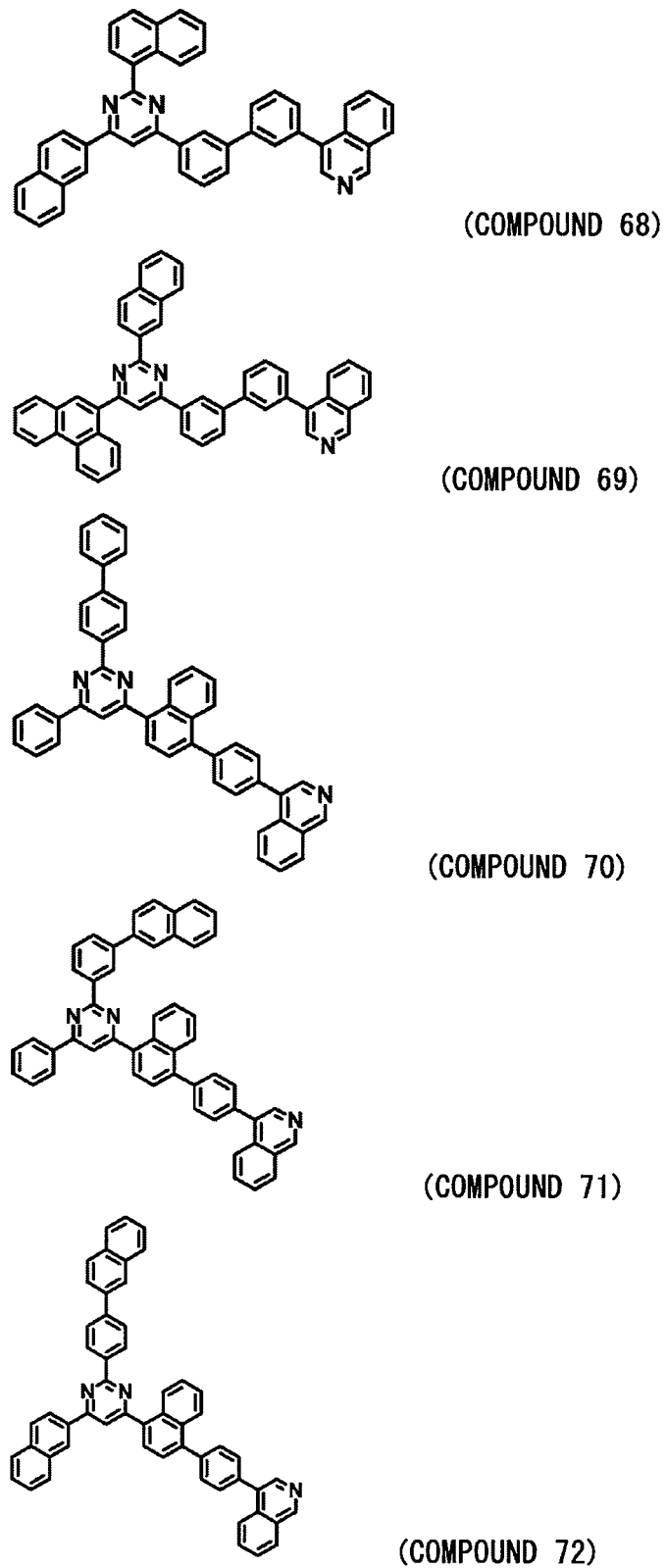
FIG. 14 A diagram showing a compound 68 to a compound 72 which are pyrimidine derivatives of the present invention.
Figure 15:
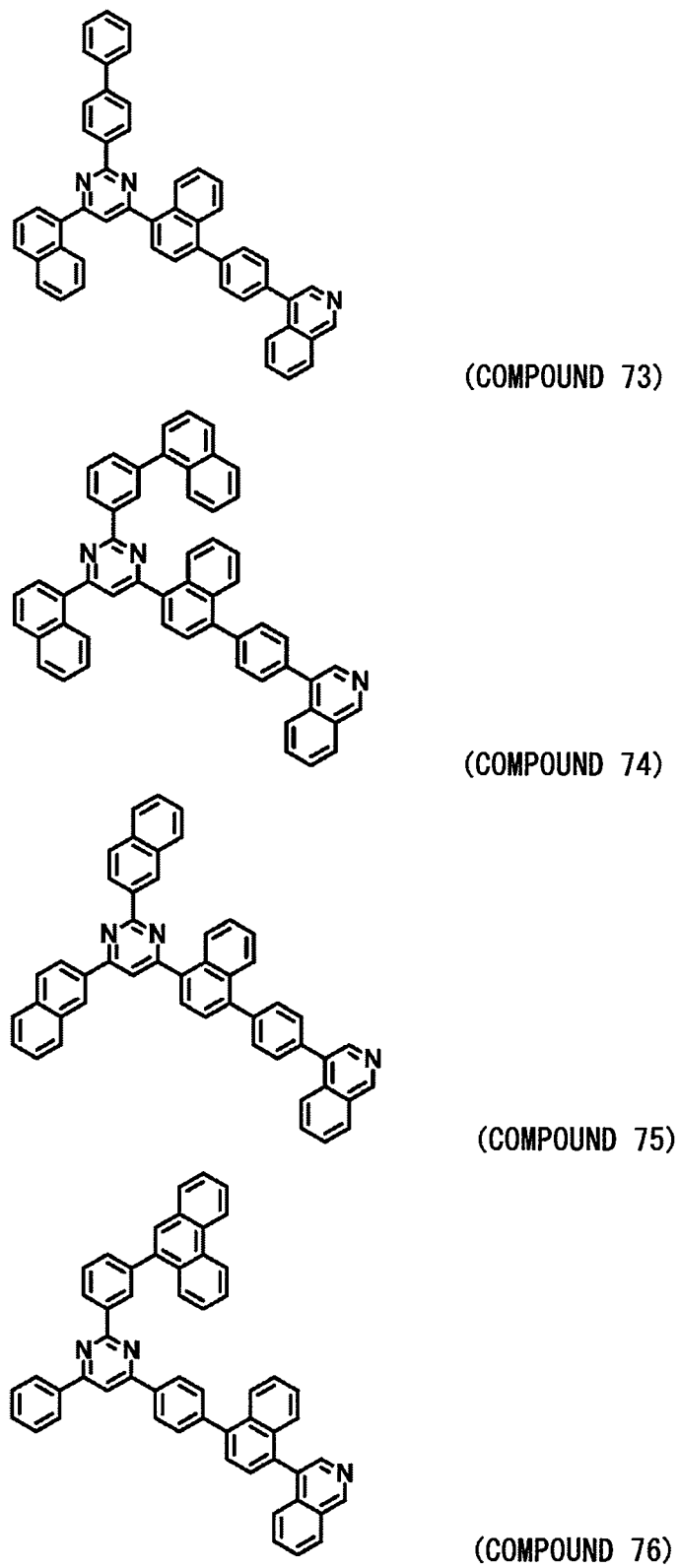
FIG. 15 A diagram showing a compound 73 to a compound 76 which are pyrimidine derivatives of the present invention.
Figure 16:
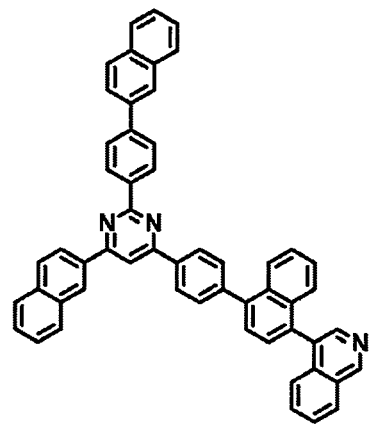
FIG. 16 A diagram showing a compound 77 to a compound 80 which are pyrimidine derivatives of the present invention.
Figure 16:
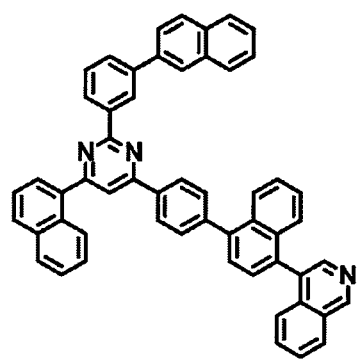
Figure 16:
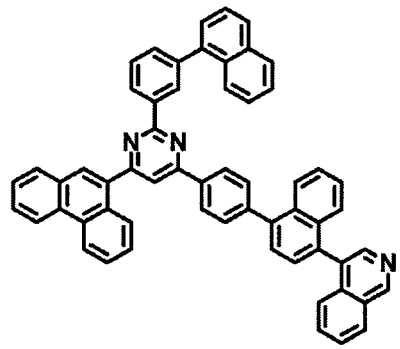
Figure 16:
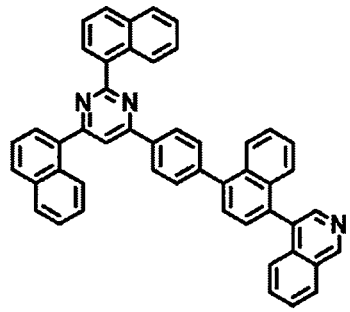
Figure 17:
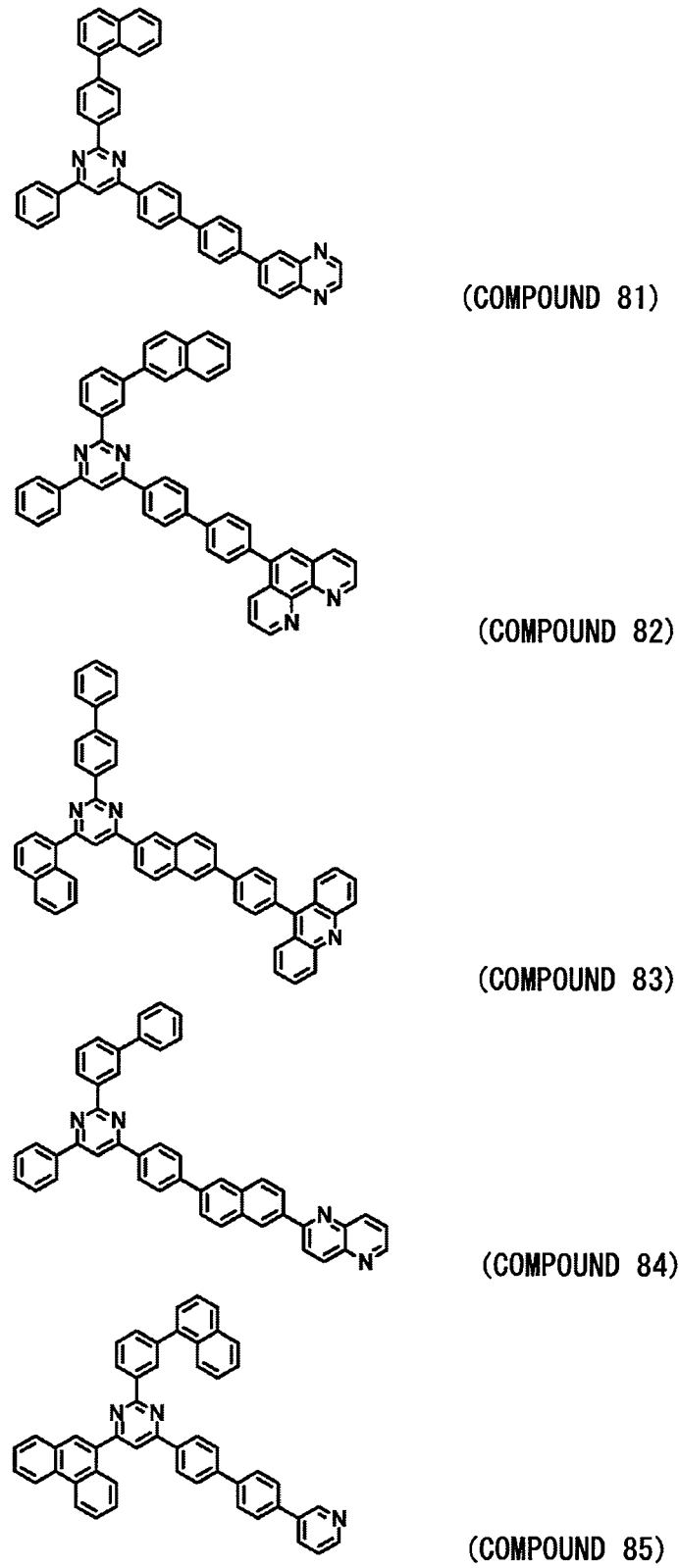
FIG. 17 A diagram showing a compound 81 to a compound 85 which are pyrimidine derivatives of the present invention.
Figure 18:
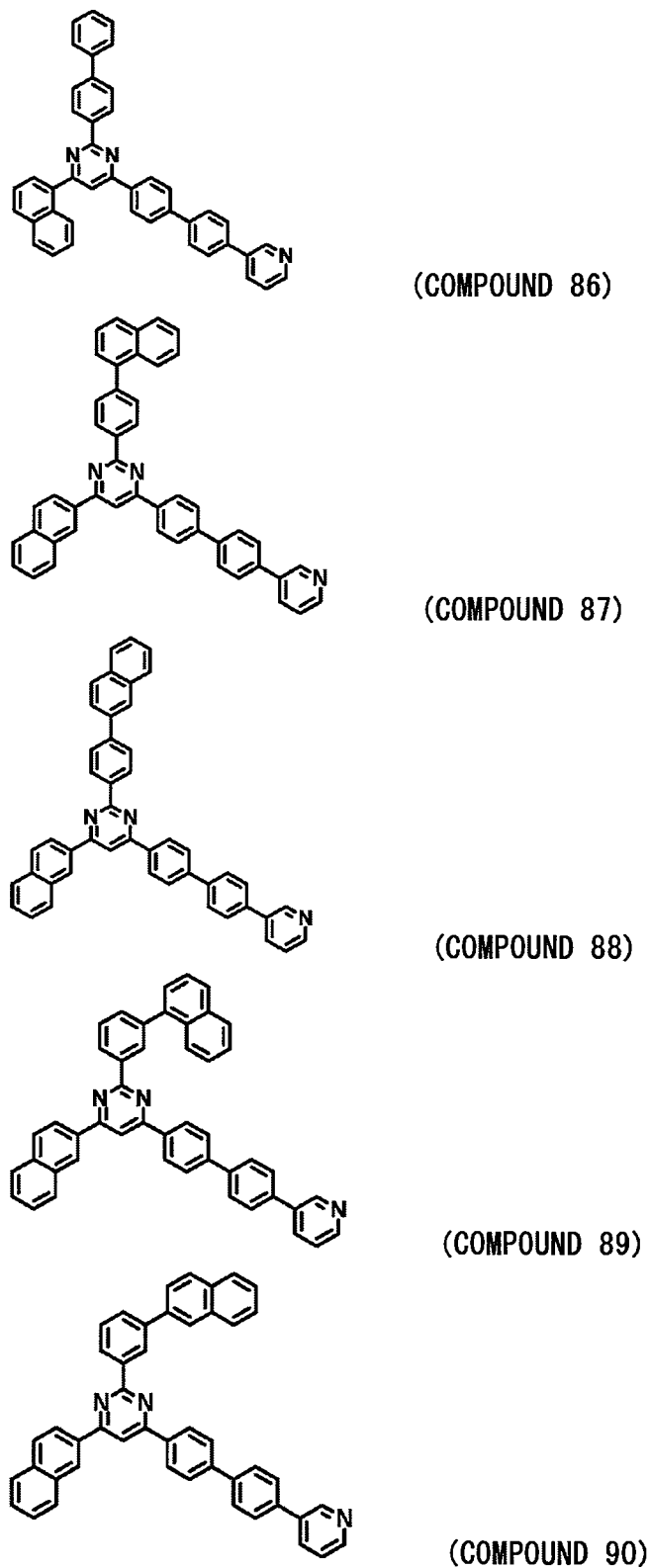
FIG. 18 A diagram showing a compound 86 to a compound 90 which are pyrimidine derivatives of the present invention.
Figure 19:
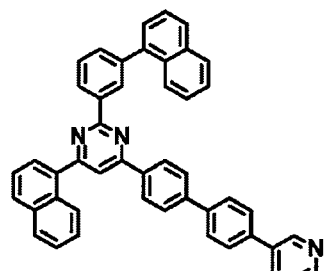
FIG. 19 A diagram showing a compound 91 to a compound 95 which are pyrimidine derivatives of the present invention.
Figure 19:
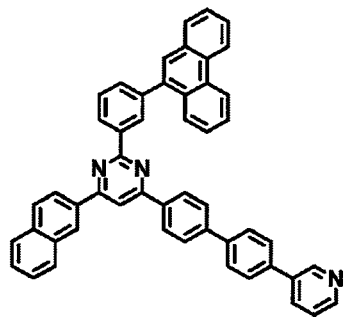
Figure 19:
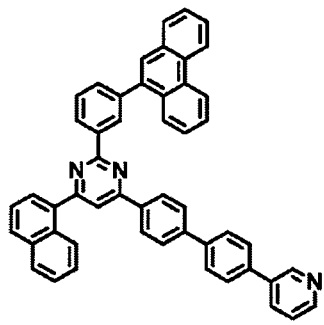
Figure 19:
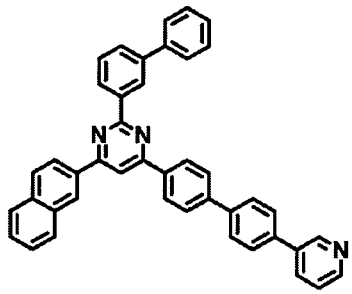
Figure 19:
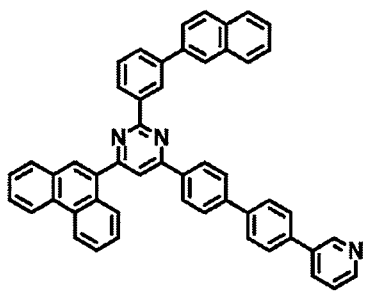
Figure 20:
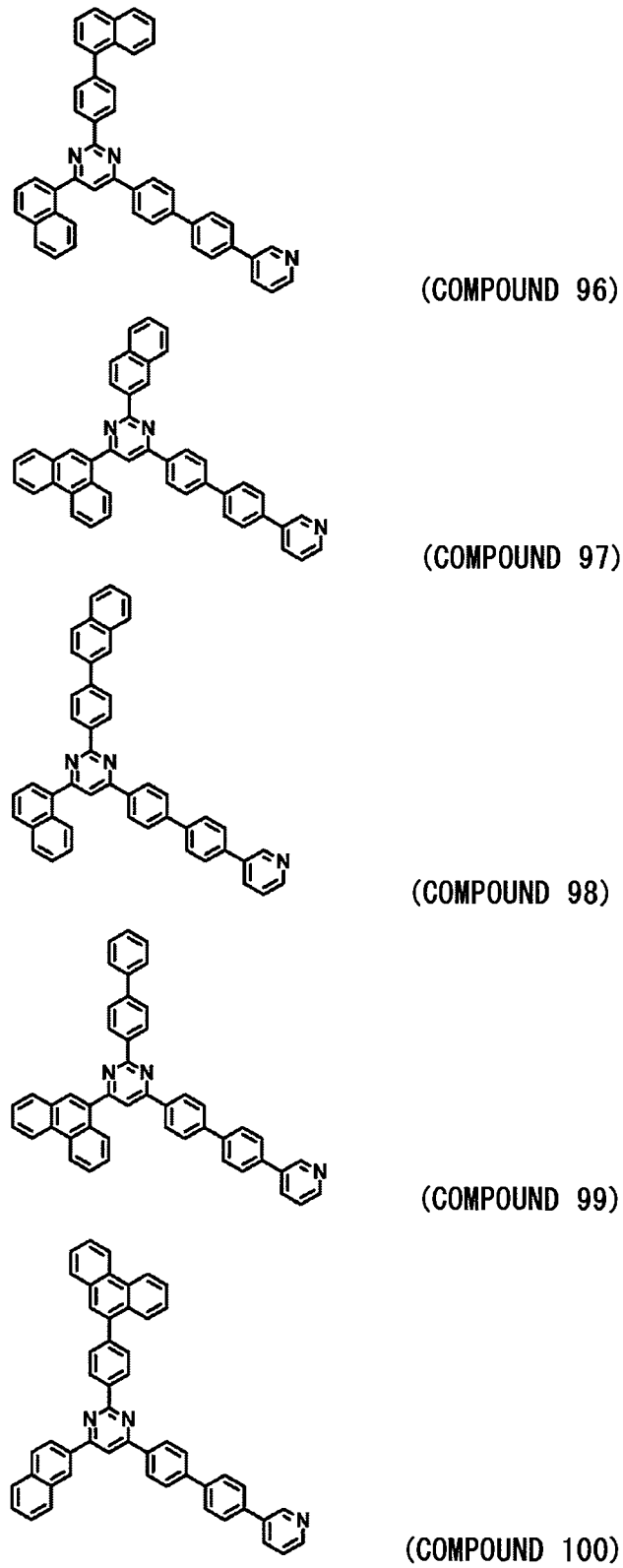
FIG. 20 A diagram showing a compound 96 to a compound 100 which are pyrimidine derivatives of the present invention.
Figure 21:
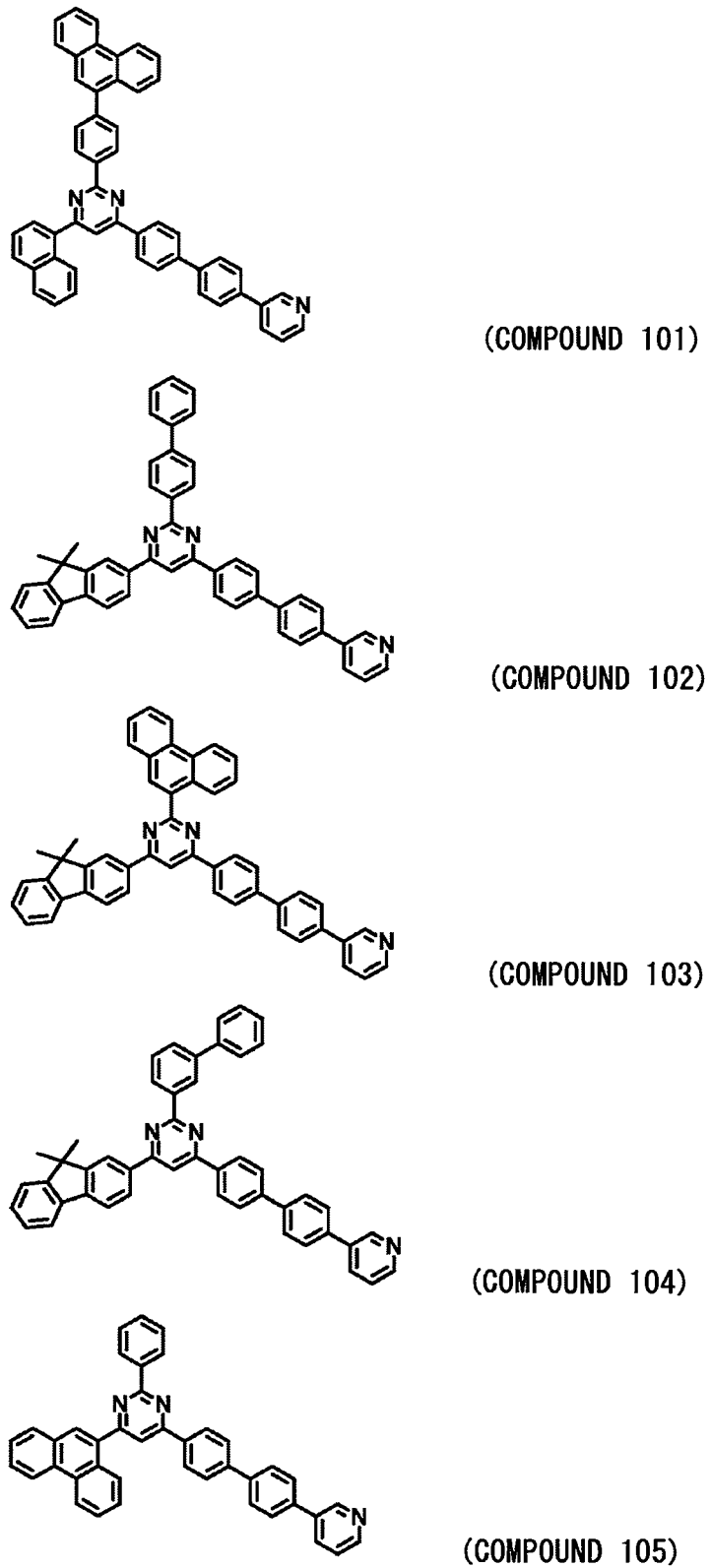
FIG. 21 A diagram showing a compound 101 to a compound 105 which are pyrimidine derivatives of the present invention.
Figure 22:
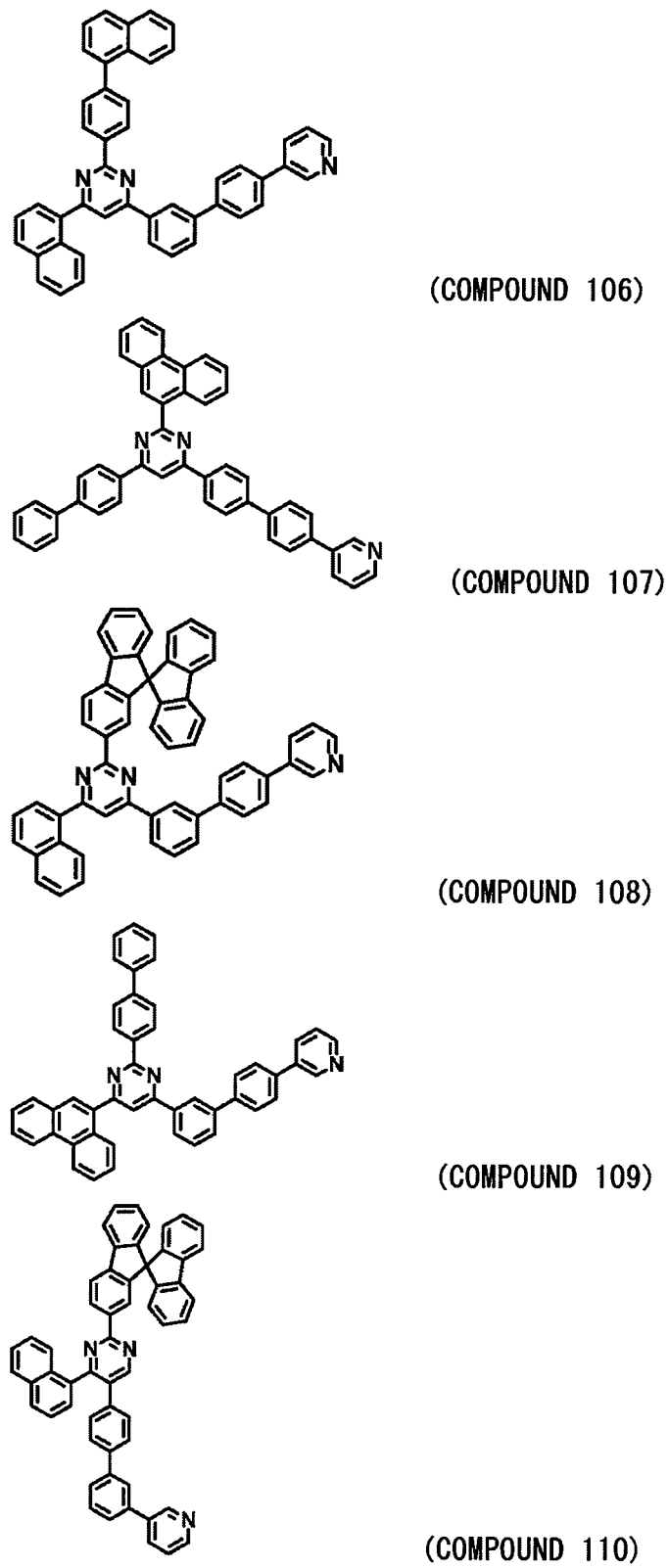
FIG. 22 A diagram showing a compound 106 to a compound 110 which are pyrimidine derivatives of the present invention.
Figure 23:
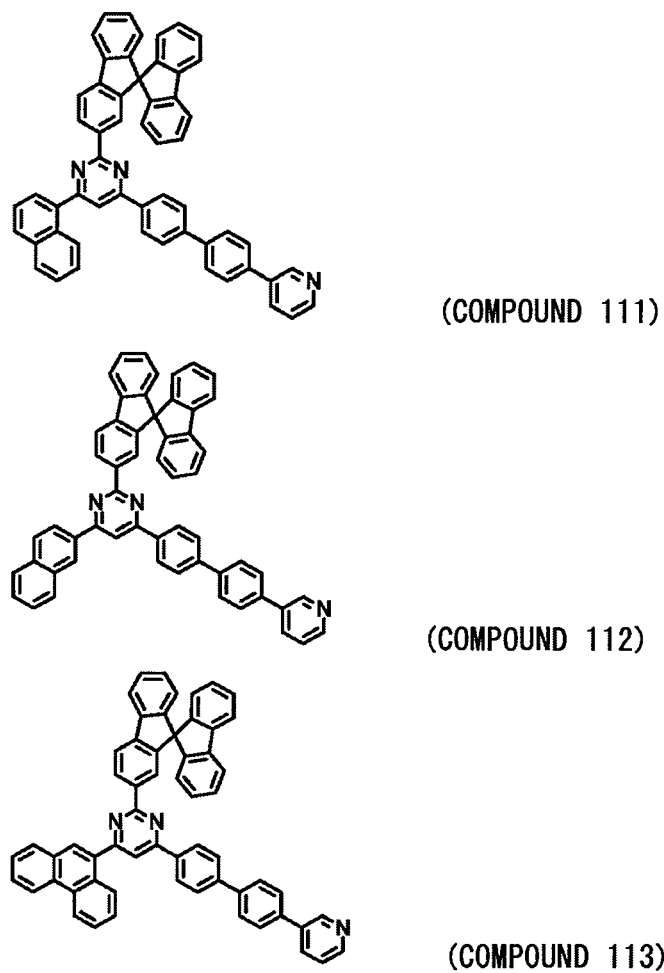
FIG. 23 A diagram showing a compound 111 to a compound 113 which are pyrimidine derivatives of the present invention.

The pyrimidine derivatives of the present invention are novel compounds having a pyrimidine ring structure and are represented by the following general formula (1).

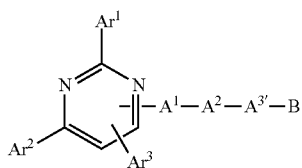

(1)

Preferably, the pyrimidine derivatives of the present invention have the structure represented by either the following general formula (1-1) or the general formula (1-2).

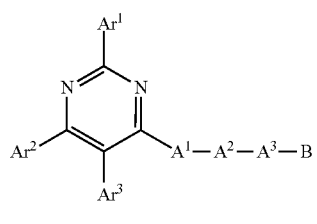

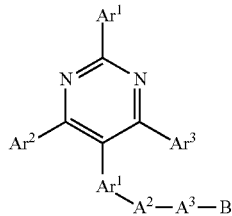

In the above general formulas (1), (1-1) and (1-2), $Ar^1$ and $Ar^2$ are, respectively, aromatic hydrocarbon groups or condensed polycyclic aromatic groups, $Ar^3$ is a hydrogen atom, an aromatic hydrocarbon group or a condensed polycyclic aromatic group, $A^1$ and $A^2$ are, respectively, divalent aromatic hydrocarbon groups or divalent condensed polycyclic aromatic groups, $A^3$ is a divalent aromatic hydrocarbon group, a divalent condensed polycyclic aromatic group, or a single bond, and B is an aromatic heterocyclic group.

<$Ar^1$ to $Ar^3$>

As the aromatic hydrocarbon groups or the condensed polycyclic aromatic groups represented by $Ar^1$ to $Ar^3$, there can be concretely exemplified phenyl group, biphenylyl group, terphenylyl group, tetrakisphenyl group, styryl group, napthyl group, antracenyl group, acenaphthenyl group, phenanthrenyl group, fluorenyl group, indenyl group, pyrenyl group, perylenyl group, fluoranthenyl group, triphenylenyl group, spirobifluorenyl group and the like.

The aromatic hydrocarbon groups or the condensed polycyclic aromatic groups represented by $Ar^1$ to $Ar^3$ may not have been substituted, or may have a substituent. As the substituent, there can be exemplified the following groups in addition to deuterium atom, cyano group and nitro group.

Halogen atoms such as fluorine atom, chlorine atom, bromine atom and iodine atom;

Alkyl groups having 1 to 6 carbon atoms, such as methyl group, ethyl group, n-propyl group, isopropyl group, n-butyl group, isobutyl group, tert-butyl group, n-pentyl group, isopentyl group, neopentyl group and n-hexyl group;

Alkyloxy groups having 1 to 6 carbon atoms, such as methyloxy group, ethyloxy group and propyloxy group;

Alkenyl groups, such as vinyl group and allyl group;

Aryloxy groups such as phenyloxy group and tollyloy group;

Arylalkyloxy groups such as benzyloxy group and phenetyloxy group;

Aromatic hydrocarbon groups or condensed polycyclic aromatic groups such as phenyl group, biphenylyl group, terphenylyl group, naphthyl group, anthracenyl group, phenanthrenyl group, fluorenyl group, indenyl group, pyrenyl group, perylenyl group, fluoranthenyl group, triphenylenyl group, spirobifluorenyl group and acenaphthenyl group;

Aromatic heterocyclic group such as pyridyl group, furanyl group, thienyl group, furyl group, pyrolyl group, quinolyl group, isoquinolyl group, benzofuranyl group, benzothienyl group, indolyl group, carbazolyl group, benzoxazolyl group, benzthiazolyl group, quinoxalyl group, benzimidazolyl group, pyrazolyl group, dibenzofuranyl group, dibenzothienyl group and carbolynyl group;

Arylvinyl groups such as styryl group and naphthylvinyl group; and

Acyl groups such as acetyl group and benzoyl group. The alkyl groups having 1 to 6 carbon atoms, the alkenyl groups and the alkyloxy groups having 1 to 6 carbon atoms may be straight chains or may have a branched form. The above substituents may not have been substituted, or may have been substituted with the substituents described above. The above substituents may be independent from each other and may not form any ring, but may, further, be bonded to each other via a single bond, via a substituted or unsubstituted methylene group, or via an oxygen atom or a sulfur atom to form a ring.

Preferred examples of $Ar^1$ are phenyl group and condensed polycyclic aromatic group and, more preferably, are phenyl group, biphenylyl group, naphthyl group, anthracenyl group, acenaphthenyl group, phenanthrenyl group, fluorenyl group, indenyl group, pyrenyl group, perylenyl group, fluoranthenyl group, triphenylenyl group and spirobifluorenyl group, and, specifically preferably, are phenyl group, biphenylyl group, naphthyl group, anthracenyl group, acenaphthenyl group, phenanthrenyl group and spirobifluorenyl group. Here, $Ar^1$ may not have been substituted or may have a substituent. From the standpoint of anisotropy of the molecule as a whole, however, $Ar^1$ that has a substituent should have 6 to 25 carbon atoms as a whole and, more preferably, 6 to 20 carbon atoms as a whole. As $Ar^1$ having a substituent, it is desired to use phenyl group. As the substituent, here, it is desired to use a condensed polycyclic aromatic group and, concretely, naphthyl group, anthracenyl group, acenaphthenyl group, phenanthrenyl group, pyrenyl group, fluoranthenyl group or triphenylenyl group. If $Ar^1$ is a substituted phenyl group, the substituent may have a further substituent. Preferably, however, the substituent has no further substituent. A preferred example of $Ar^1$ that has no substituent is a condensed polycyclic aromatic group.

Preferred examples of $Ar^2$ are unsubstituted aromatic hydrocarbon group, substituted or unsubstituted condensed polycyclic aromatic group and 9,9-dimethylfluorenyl group. Concretely speaking, preferred examples of $Ar^2$ are unsubstituted phenyl group or biphenylyl group; substituted or unsubstituted naphthyl group, anthracenyl group, acenaphthenyl group, phenanthrenyl group, indenyl group, pyrenyl group, perylenyl group, fluoranthenyl group and triphenylenyl group; and 9,9-dimethylfluorenyl group. More preferred examples of $Ar^2$ are unsubstituted phenyl group or biphenylyl group; unsubstituted naphthyl group, anthracenyl group, phenanthrenyl group, pyrenyl group, fluoranthenyl group and triphenylenyl group; and 9,9-dimethylfluorenyl group.

Preferred examples of $Ar^3$ include a hydrogen atom and a phenyl group having a substituent. A more preferred example of $Ar^3$ is a hydrogen atom. As the substituent of the "phenyl group having a substituent" which is a preferred form of $Ar^3$, there can be exemplified aromatic hydrocarbon groups such as phenyl group, biphenylyl group, and terphenyl group; or condensed polycyclic aromatic groups such as naphthyl group, anthracenyl group, acenaphthenyl group, phenanthrenyl group, fluorenyl group, indenyl group, pyrenyl group, perylenyl group, fluoranthenyl group, and triphenylenyl group. More preferred examples are phenyl group, naphthyl group, anthracenyl group, phenanthrenyl group, pyrenyl group, fluoranthenyl group and triphenylenyl group.

$Ar^1$ and $Ar^2$ may be the same groups but are preferably different groups from the standpoint of stability of the form of thin film. The case where $Ar^1$ and $Ar^2$ are the different groups includes the case where they are bonded to the pyrimidine ring at different positions, the case where they have different substituents or the case where they have substituents and the substituents bond to $Ar^1$ and $Ar^2$ at different positions.

$Ar^2$ and $Ar^a$ may be the same groups. The compound, however, tends to be crystallized because the molecules as a whole acquire good symmetry. From the standpoint of stability of the thin film, therefore, it is desired that $Ar^2$ and $Ar^3$ are the different groups.

<$A^1$ to $A^3$>

The divalent aromatic hydrocarbon group or the divalent condensed polycyclic aromatic group represented by $A^1$ to $A^3$ is formed by removing two hydrogen atoms from the aromatic hydrocarbon or the condensed polycyclic aromatic ring. In this case, concrete examples of the aromatic hydrocarbon or the condensed polycyclic aromatic ring include benzene, biphenyl, terphenyl, tetrakisphenyl, styrene, naphthalene, anthracene, acenaphthalene, fluorene, phenathrene, indane, pyrene and triphenylene.

The aromatic hydrocarbon groups or the condensed polycyclic aromatic groups represented by $A^1$ to $A^3$ may not have been unsubstituted, or may have a substituent. As the substituent, there can be exemplified those that are the same as those exemplified above as the substituents that may be possessed by the aromatic hydrocarbon groups or the condensed polycyclic aromatic groups represented by $Ar^1$ to $Ar^3$. The forms acquired by the substituents are also the same.

$A^1$ or $A^2$ is, preferably, a divalent group (phenylene group) formed by removing two hydrogen atoms from benzene or a divalent group (naphthylene group) formed by removing two hydrogen atoms from naphthalene. More preferably, either $A^1$ or $A^2$ is a phenylene group and the other one is a naphthylene group, or $A^1$ and $A^2$ are both phenylene groups from such a standpoint that the sublimation temperature does not become too high in case the organic EL device is formed by the vacuum evapolation method.

$A^3$ is, preferably, a single bond since the sublimation temperature does not become too high in case the organic EL device is formed by the vacuum evaporation method.

<B>

Concrete examples of the aromatic heterocyclic group represented by B include triazinyl group, pyridyl group, pyrimidinyl group, furyl group, pyrolyl group, thienyl group, quinolyl group, isoquinolyl group, benzofuranyl group, benzothenyl group, indolyl group, carbazolyl group, benzoxazolyl group, benzothiazolyl group, quinoxalynyl group, benzoimidazolyl group, pyrazolyl group, dibenzofuranyl group, dibenothienyl group, napthylydinyl group, phenanthrolynyl group, acridinyl group, carbolinyl group, bipyridyl group, terpyridyl group, pyradinyl group, imidazolyl group, quinazolinyl group, benzotriazolyl group, benzothiadiazolyl group, pyridopyrolyl group, pyridoimidazolyl group, pyridotriazolyl group, phenadinyl group, phenoxadinyl group, phenothiadinyl group and the like.

The aromatic heterocyclic group represented by B may not have been substituted, or may have a substituent. As the substituent, there can be exemplified those which are the same as the above-mentioned substitutents that may be possessed by the aromatic hydrocarbon groups or the condensed polycyclic aromatic groups represented by $Ar^1$ to $Ar^3$. The same also holds for the forms that are assumed by the substituents.

As the group B, nitrogen-containing heterocyclic groups such as triazinyl group, pyridyl group, pyrimidinyl group, pyrolyl group, quinolyl group, isoquinolyl group, indolyl group, carbazolyl group, benzoxazolyl group, benzothiazolyl group, quinoxalynyl group, benzoimidazolyl group, pyrazolyl group, naphthylydinyl group, phenanthrolynyl group, acrydinyl group and carbolinyl group are preferable. Triazinyl group, pyridyl group, pyrimidinyl group, quinolyl group, isoquinolyl group, indolyl group, quinoxalinyl group, benzoimidazolyl group, naphthyridinyl group, phenanthrolinyl group or acridinyl group is more preferable. Pyridyl group, pyrimidinyl group, quinolyl group, isoquinolyl group, indolyl group, quinoxalinyl group, benzimidazolyl group, phenanthrolinyl group or acridinyl group is most preferable.

Or, as the group B, pyridyl group, bipyridyl group, terpyridyl group, pyrimidinyl group, pyradinyl group, triazinyl group, pyrolyl group, pyrazolyl group, imidazolyl group, furyl group, thienyl group, quinolyl group, isoquinolyl group, quinoxalinyl group, quinazolinyl group, naphthyridinyl group, indolyl group, benzimidazolyl group, benzotriazolyl group, benzofuranyl group, benzothienyl group, benzoxazolyl group, benzothiazolyl group, benzothiadiazolyl group, pyridopyrolyl group, pyridoimidazolyl group, pyridotriazolyl group, acridinyl group, phenadinyl group, phenanthrolinyl group, phenoxadinyl group, phenothiadinyl group, carbazolyl group, carbolinyl group, dibenzofuranyl group or dibenzothienyl group is preferable.

FIGS. 1 to 23 concretely show the preferred compounds among the pyrimidine derivatives of the present invention. The invention, however, is in no way limited to these compounds only. Here, among the compounds shown in FIGS. 1 to 23, what correspond to the formula (1-1) are the compounds 1 to 109 and compounds 111 to 113, and what corresponds to the formula (1-2) is the compound 110.

<Method of Preparation>

The pyrimidine derivatives of the present invention can be prepared by a known method. For example, the pyrimidine derivatives can be prepared as described below. Namely, a 2,4,6-trichloropyrimidine and an arylboronic acid or an arylboronic acid ester having a group corresponding to the group $Ar^2$ are subjected to the Suzuki coupling reaction to synthesize a pyrimidine (hereinafter called fourth position-substituted pyrimidine) that is substituted at its fourth position with an aryl group that corresponds to the group $Ar^2$. Thereafter, the fourth position-substituted pyrimidine and the arylboronic acid or the arylboronic acid ester having a heteroaryl group as a substituent that has the group corresponding to the group $A^1$-$A^2$-$A^3$-B, are subjected to the Suzuki coupling reaction. Thus the aryl group having, as a substituent, the heteroaryl group that corresponds to the group A$^1$-A$^2$-A$^3$-B is introduced to the sixth portion of the pyrimidine ring. The pyrimidine thus obtained is called fourth position- and sixth position-substituted pyrimidine. Thereafter, the fourth position- and sixth position-substituted pyrimidine and the arylboronic acid or the arylboronic acid ester having the group corresponding to Ar$^1$ are subjected to the Suzuki coupling reaction to thereby synthesize the pyrimidine derivative of the present invention.

Here, if there is used a trihalogenated pyrimidine having a halogen atom (e.g., chloro group) substituted at a different position, then there can be synthesized a pyrimidine derivative of the present invention having the substituent at a different position.

It is, further, allowable to synthesize the pyrimidine derivatives of the present invention having substituents at different positions by using a monohalogenated pyrimidine or a dihalogenated pyrimidine, similarly introducing the aryl group having, as a substituent, the aryl group and/or the heteroaryl group, conducting the halogenation with an N-bromosuccinic acid imide to thereby introduce a halogen group into the pyrimidine ring and, thereafter, conducting the Suzuki coupling reaction in order to introduce the aryl group that has the aryl group and/or the heteroaryl group as a substituent.

The synthesized compounds are refined by column chromatography, by the adsorption refining method using silica gel, activated carbon or activated clay, by the recrystallization method or the crystallization method using a solvent or by the sublimation purification method or the like. Further, the compounds are identified by the NMR analysis.

Work function and glass transition temperature (Tg) can be measured as physical properties. The work function is an index for blocking holes. The work function can be measured by forming a thin film with a thickness of 100 nm on an ITO substrate and using an ionization potential measuring device (Model PYS-202, manufactured by Sumitomo Heavy Industries, Ltd.). Further, the glass transition temperature serves as an index of stability of the thin film. The glass transition temperature (Tg) is measured by using a powder and a high-sensitivity differential scanning calometer (DSC 3100SA manufactured by Bruker AXS K.K.).

<Organic EL Devices>

The pyrimidine derivative of the present invention can be favorably used as a material of an organic layer in the organic EL device. The organic EL device formed by using the pyrimidine derivative of the invention (hereinafter often called organic EL device of the invention) assumes a structure in which an anode, a hole transport layer, a luminous layer, an electron transport layer and a cathode are formed successively on a substrate such as a glass substrate or a transparent plastic substrate (e.g., polyethylene terephthalate substrate).

The organic EL device of the present invention may, further, have a hole injection layer between the anode and the hole transport layer. Or, the organic EL device may have an electron injection layer between the electron transport layer and the cathode, may have an electron-blocking layer between the luminous layer and the hole transport layer, or may have a hole blocking layer between the luminous layer and the electron transport layer.

In the organic EL device of the present invention, some organic layers can be omitted. For instance, there can be formed a layer that serves both as the hole blocking layer and the electron transport layer, a layer that serves both as the hole injection layer and the hole transport layer, and a layer that serves both as the electron injection layer and the electron transport layer.

In the organic EL device of the invention, further, the organic layer can be a lamination of two or more layers having the same function. Concretely, the hole transport layer can be a lamination of two layers, the luminous layer can be a lamination of two layers, and the electron transport layer can be a lamination of two layers.

Figure 27:
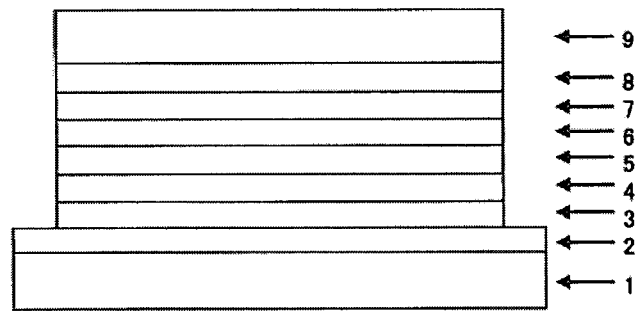
FIG. 27 A view illustrating a constitution of an organic EL device of the present invention.

FIG. 27, for example, illustrates the constitution of layers of the organic EL device having a transparent anode 2, a hole injection layer 3, a hole transport layer 4, a luminous layer 5, a hole blocking layer 6, an electron transport layer 7, an electron injection layer 8 and a cathode 9 formed in this order on a glass substrate 1. The layers constituting the organic EL device of the invention will now be described below.

(Anode 2)

As the anode 2, there is used an electrode material having a large work function, such as ITO or gold.

(Hole Injection Layer 3)

The hole injection layer 3 is provided between the cathode 2 and the hole transport layer 4. As the hole injection layer 3, there can be used a known material such as porphyline compound as represented by copper phthalocyanine; triphenylamine derivative of the star burst type; triphenylamine trimer and a triphenylamine tetramer, e.g., arylamine compound having not less than three triphenylamine structures in the molecules, the triphenylamine structures being bonded to each other via a single bond or a divalent group having no hetero atom; an acceptor-type heterocyclic compound such as hexacyanoazatriphenylene; and a coating-type polymer material.

These materials can be used in a single kind to form the film but can also be used in a mixture of a plurality of materials to form the film. In addition to using the materials that are usually used for forming the hole injection layer, it is also allowable to use a material P-doped with a trisbromophenylaminehexachloroantimony, a radialene derivative (see International Laid-Open WO2014/009310) or the like or a polymer compound having a benzidine derivative as its partial structure such as TPD.

The hole injection layer 3 can be obtained if a thin film is formed by using the above materials relying on a known method such as the vacuum evaporation method, the spin-coating method or the ink-jet method. The layers described below, too, can similarly be obtained by forming thin films by the known method such as the vacuum evaporation, the spin-coating method or the ink-jet method.

(Hole Transport Layer 4)

The hole transport layer 4 is provided between the anode 2 and the luminous layer 5. For the hole transport layer 4, there can be used the following materials.

Benzidine derivatives such as,

N,N'-Diphenyl-N,N'-di(m-tolyl) benzidine (TPD),

N,N'-Diphenyl-N,N'-di(α-naphthyl) benzidine (NPD),

N,N,N',N'-Tetrabiphenylylbenzidine;

1,1-Bis[(di-4-tolylamino)phenyl] cyclohexane (TAPC); and

Various triphenylamine trimers and tetramers.

These materials can be used in a single kind to form the film but can also be used in a mixture of a plurality of materials to form the film. Further, the hole transport layer 4 may have a single-layer structure or a structure of a plurality of layers.

In addition to using the materials that are usually used for forming the hole transport layer 4, it is also allowable to use a material P-doped with a trisbromophenylaminehexachloroantimony, a radialene derivative (see International Laid-Open WO2014/009310) or the like or a polymer compound having a benzidine derivative as its partial structure such as TPD.

In the invention, it is allowable to use coating-type polymer materials such as poly(3,4-ethylenedioxythiophene) (PEDOT)/poly(styrene sulfonate) (PSS) for forming the hole injection layer 3 and/or the hole transport layer 4.
(Electron-Blocking Layer)

Though not illustrated in FIG. 27, an electron-blocking layer can be provided between the hole transport layer 4 and the luminous layer 5. For the electron-blocking layer, there can be used a known compound having the electron-blocking action. As the known compound, there can be exemplified the following compounds.
Carbazole derivatives such as,
4,4',4''-Tri(N-carbazolyl)triphenylamine (TCTA);
9,9-Bis[4-(carbazole-9-yl)phenyl]fluorene;
1,3-Bis(carbazole-9-yl)benzene (mCP);
2,2-Bis(4-carbazole-9-ylphenyl)adamantane (Ad-Cz);
Compounds having a triphenylsilyl group and a triarylamine structure, such as,
9-[4-(Carbazole-9-yl)phenyl]-9-[4-(triphenylsilyl) phenyl]-9H-fluorene;
Monoamine compound having a high electron blocking property; and
Various triphenylamine dimers.

These materials can be used in a single kind to form the film but can also be used in a mixture of a plurality of materials to form the film. Further, the electron-blocking layer may have a single-layer structure or a structure of a plurality of layers.
(Luminous Layer 5)

For the luminous layer 5, there can be used the pyrimidine derivatives of the present invention as well as any other known luminous materials. As the known luminous materials, there can be exemplified various metal complexes like metal complexes of quinolynol derivatives such as $Alq_3$; anthracene derivatives; bisstyrylbenzene derivatives; pyrene derivatives; oxazole derivatives; polyparaphenylenevinylene derivatives; and the like.

It is also allowable to constitute the luminous layer 5 by using a host material and a dopant material. As the host material, there can be used thiazole derivatives; benzimidazole derivatives; polydialkylfluorene derivatives; and heterocyclic compounds having an indole ring as a partial structure of the condensed ring in addition to using the pyrimidine derivatives of the present invention and the above-mentioned luminous materials.

As the dopant material, there can be used pyrine derivatives; anthracene derivatives; quinacridone, cumalin, rubrene, perylene and derivatives thereof; benzopyran derivatives; rhodamine derivatives; aminostyryl derivatives; and spirobisfluorene derivatives.

As the luminous material, it is also allowable to use a phosphorescent luminous body. As the phosphorescent luminous body, there can be used a phosphorescent luminous body of a metal complex such as of iridium or platinum. Concretely, there can be used a green phosphorescent luminous body such as $Ir(ppy)_3$; a blue phosphorescent luminous body such as Flrpic or $Flr_6$; and a red phosphorescent luminous body such as $Btp_2Ir(acac)$.

As the host material, in this case, there can be used the following hole injection transporting host materials:
Carbazole derivatives such as 4,4'-di(N-carbazolyl)biphenyl (CBP), TCTA, mCP;
Heterocyclic compounds having an indole ring as a partial structure of the condensed ring.
Or, the following electron transporting host materials can be used:
p-Bis(triphenylsilyl)benzene (UGH2);
2,2',2''-(1,3,5-phenylene)-tris(1-phenyl-1H-benzimidazole) (TPB1).

Organic EL devices of high performance can be fabricated by using the above host materials.

To avoid the concentration quenching, the host material is desirably doped with the phosphorescent luminous material in an amount in a range of 1 to 30% by weight relative to the whole luminous layer relying on the vacuum coevaporation.

As the luminous material, further, it is also allowable to use a material that emits delayed fluorescence, such as CDCB derivative like PIC-TRZ, CC2TA, PXZ-TRZ or 4CzIPN.

These materials can be used in a single kind to form the film but can also be used in a mixture of a plurality of materials to form the film. Further, the luminous layer 5 may have either a single-layer structure or a structure of a plurality of layers.
(Hole Blocking Layer 6)

The hole blocking layer 6 can also be formed between the luminous layer 5 and the electron transport layer 7. For the hole blocking layer 6, there can be used the pyrimidine derivatives of the present invention as well as any other known compounds having a hole blocking action. As the known compound having the hole blocking action, there can be exemplified phenanthrolene derivatives such as bathocuproin (BCP), metal complexes of quinolynol derivatives such as BAlq, as well as various rare earth complexes, oxazole derivatives, triazole derivatives, triazine derivatives and the like.

These materials may also be used as the material of the electron transport layer 7. These materials may be used alone to form the film or may be used in a mixture of a plurality of materials to form the film. Further, the hole blocking layer 6 may have a single-layer structure or a structure of a plurality of layers.
(Electron Transport Layer 7)

For the electron transport layer 7, there can be used the pyrimidine derivatives of the present invention as well as various metal complexes like metal complexes of quinolinol derivatives such as $Alq_3$, BAlq; triazole derivatives; triazine derivatives; oxadiazole derivatives; pyridine derivatives; benzimidazole derivatives; thiadiazole derivatives; anthracene derivatives; carbodiimide derivatives; quinoxaline derivatives; pyridoindole derivatives; phenanthroline derivatives; silole derivatives; and the like.

For the electron transport layer 7, there can be used the materials that are usually used for the electron transport layer as well as the materials that are N-doped with a metal such as cesium.

These materials may be used alone to form the film or may also be used in a mixture of a plurality of materials to form the film. Moreover, the electron transport layer 7 may have a single-layer structure or a structure of a plurality of layers.
(Electron Injection Layer 8)

The electron injection layer 8 is formed between the electron transport layer 7 and the cathode 9. For the electron injection layer 8, there can be used the pyrimdine derivatives of the present invention, as well as alkali metal salts such as lithium fluoride and cesium fluoride; alkaline earth metal salts such as magnesium fluoride; metal complexes of quinolinol derivatives such as lithium quinolinol; metal oxides such as aluminum oxide; and the like. The electron injection layer 8, however, can be omitted if the electron transport layer and the cathode are preferably selected.

For the electron injection layer 8, there can be used the materials that are usually used for the electron injection layer as well as the materials that are N-doped with a metal such as cesium.
(Cathode 9)

For the cathode 9, there can be used an electrode material having a low work function, such as aluminum, or an alloy having a lower work function, such as magnesium-silver alloy, magnesium-indium alloy or aluminum-magnesium alloy.

EXAMPLES

The invention will now be concretely described by way of Examples to which only, however, the invention is in no way limited unless it does not depart from the gist and spirit of the present invention.

Example 1: Compound 1

Synthesis of 2-(biphenyl-4-yl)-4-phenyl-6-{4'-(pyridin-3-yl)biphenyl-4-yl} pyrimidine 2-Chloro-4-phenyl-6-{4'-(pyridin-3-yl)biphenyl-4-yl}pyrimidine 8.0 g,
4-Biphenylboronic acid 3.8 g,
Tetrakistriphenylphosphine 0.44 g,
Potassium carbonate 7.9 g,
Toluene 80 ml,
Tetrahydrofuran 80 ml, and
Water 40 ml,
were put into a reaction vessel purged with nitrogen, were heated and were stirred at 80° C. for 12 hours to prepare a reaction solution. The reaction solution was cooled down to room temperature, and the organic layer was picked up by the solution separation operation. Thereafter, the solution was concentrated under reduced pressure to obtain a crude product which was then refined by the column chromatography (carrier: silica gel, eluent: ethyl acetate/heptane) and was, thereafter, refined again by the recrystallization by using a mixed solvent of tetrahydrofuran/acetone. There was obtained 3.0 g of a white powder of 2-(biphenyl-4-yl)-4-phenyl-6-{4'-(pyridin-3-yl)biphenyl-4-yl}pyrimidine (compound 1) (yield, 30%).

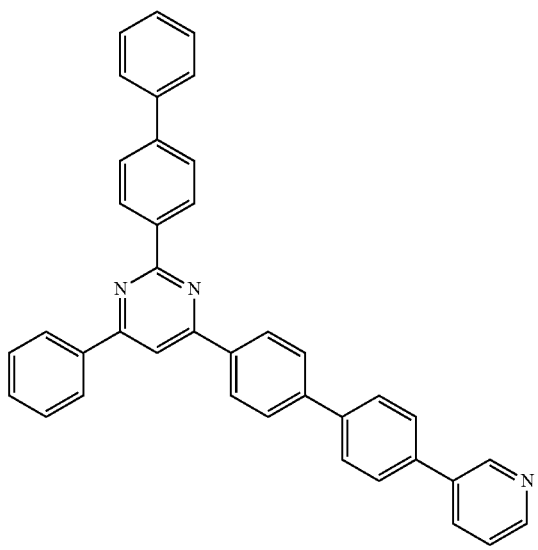

(Compound 1)

Figure 24:
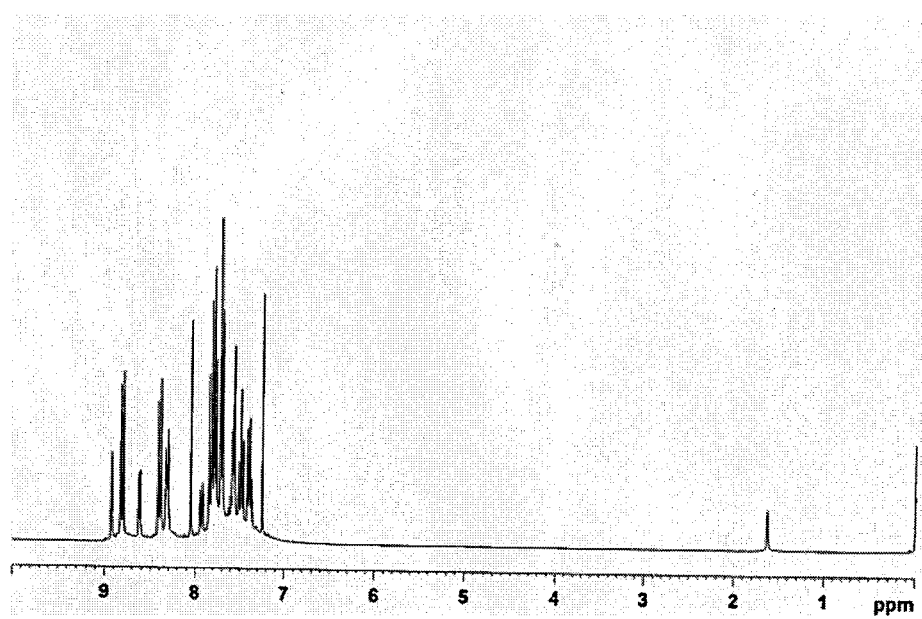
FIG. 24 A $^1$H-NMR chart of the compound (compound 1) of Example 1.

The obtained white powder was identified for its structure by the NMR. FIG. 24 shows the results of the ¹H-NMR measurement. The following 27 signals of hydrogen were detected by the ¹H-NMR (CDCl₃).

δ (ppm)=8.94 (1H)
8.83 (2H)
8.64 (1H)
8.43-8.32 (4H)
8.07 (1H)
7.97-7.35 (18H)

Example 2: Compound 2

Synthesis of 2-{4-(naphthalen-1-yl)phenyl}-4-phenyl-6-{4'-(pyridin-3-yl)biphenyl-4-yl}pyrimidine The reaction was carried out under the same conditions as in Example 1 but using
{4-(naphthalen-1-yl)phenyl}boronic acid
instead of using
4-biphenylboronic acid.
As a result, there was obtained 1.6 g of a white powder of 2-{4-(naphthalen-1-yl)phenyl}-4-phenyl-6-{4'-(pyridin-3-yl)biphenyl-4-yl}pyrimidine (compound 2) (yield, 15%).

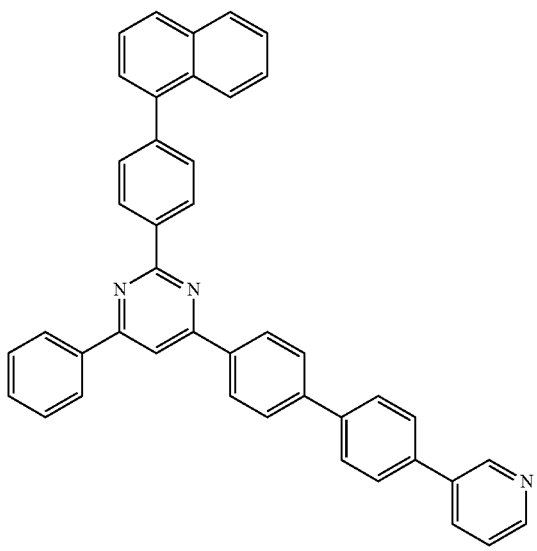

(Compound 2)

Figure 25:
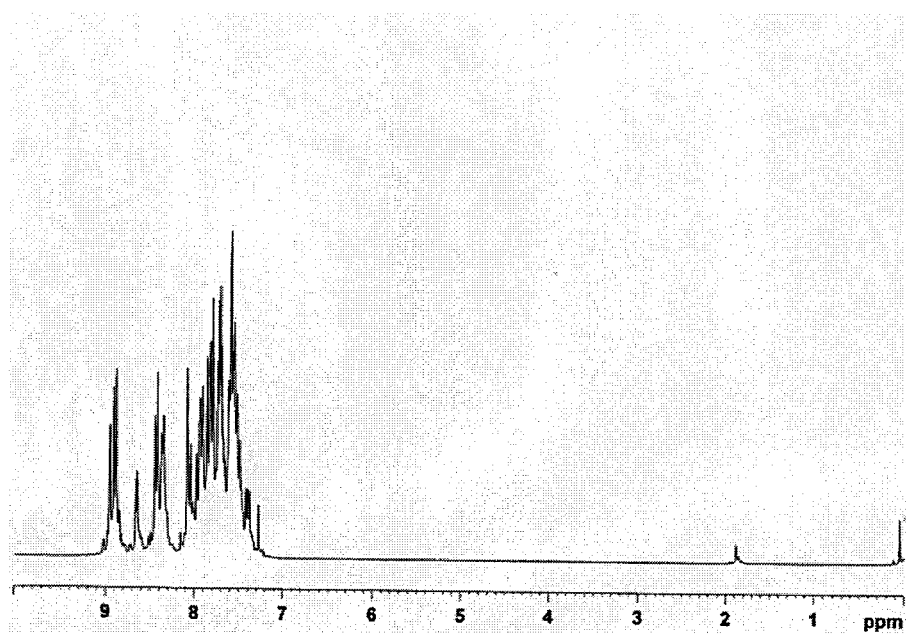
FIG. 25 A $^1$H-NMR chart of the compound (compound 2) of Example 2.

The obtained white powder was identified for its structure by the NMR. FIG. 25 shows the results of the ¹H-NMR measurement. The following 29 signals of hydrogen were detected by the ¹H-NMR (CDCl₃).

δ (ppm)=9.00-8.81 (3H)
8.65 (1H)
8.51-8.28 (4H)
8.11-7.32 (21H)

Example 3: Compound 29

Synthesis of 2,4-bis(phenanthren-9-yl)-6-{4'-(pyridin-3-yl)biphenyl-4-yl}pyrimidine The reaction was carried out under the same conditions as in Example 1 but using
2-chloro-4-(phenanthren-9-yl)-6-{4'-(pyridin-3-yl)biphenyl-4-yl}pyrimidine
instead of using
2-chloro-4-phenyl-6-{4'-(pyridin-3-yl)biphenyl-4-yl}pyrimidine, and using phenanthrene-9-boronic acid instead of using 4-biphenylboronic acid.

As a result, there was obtained 1.2 g of a white powder of 2,4-bis(phenanthren-9-yl)-6-{4'-(pyridin-3-yl)-biphenyl-4-yl}pyrimidine (compound 29) (yield, 14%).

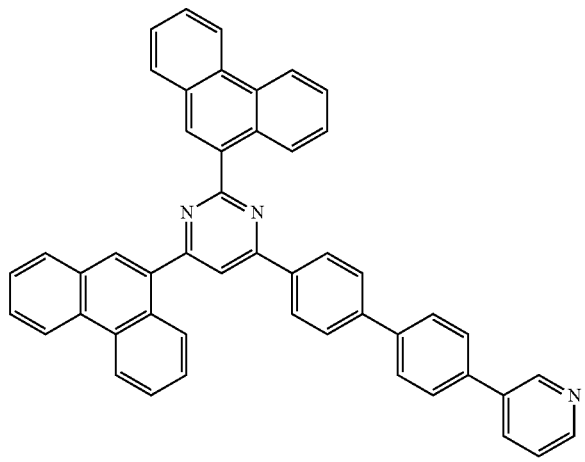

(Compound 29)

Figure 26:
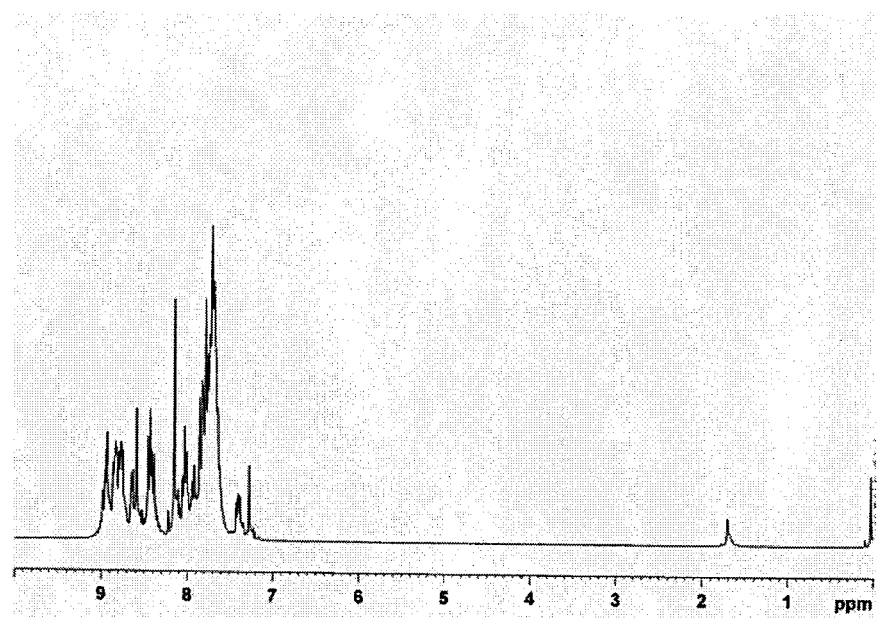
FIG. 26 A $^1$H-NMR chart of the compound (compound 29) of Example 3.

The obtained white powder was identified for its structure by the NMR. FIG. 26 shows the results of the $^1$H-NMR measurement. The following 31 signals of hydrogen were detected by the $^1$H-NMR (CDCl$_3$).

δ (ppm)=9.05-8.35 (14H)

8.25-7.52 (15H)

7.45-7.35 (2H)

Example 4: Compound 96

Synthesis of 4-(naphthalen-1-yl)-2-{4-(naphthalen-1-yl)phenyl}-6-{4'-(pyridin-3-yl)biphenyl-4-yl}pyrimidine The reaction was carried out under the same conditions as in Example 1 but using 2-chloro-4-(naphthalen-1-yl)-6-{4'-(pyridin-3-yl)biphenyl-4-yl}pyrimidine instead of using 2-chloro-4-phenyl-6-{4'-(pyridin-3-yl)biphenyl-4-yl}pyrimidine, and using 4-(naphthalen-1-yl)phenylboronic acid instead of using 4-biphenylboronic acid.

As a result, there was obtained 1.9 g of a white powder of 4-(naphthalen-1-yl)-2-{4-(naphthalen-1-yl)phenyl}-6-{4'-(pyridin-3-yl)biphenyl-4-yl}pyrimidine (compound 96) (yield, 28%).

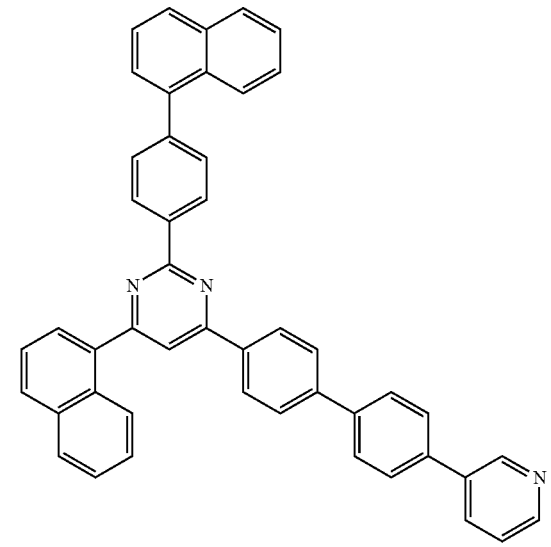

(Compound 96)

The obtained white powder was identified for its structure by the NMR. The following 31 signals of hydrogen were detected by the $^1$H-NMR (CDCl$_3$).

δ (ppm)=8.97 (1H)

8.89 (2H)

8.63 (1H)

8.51-8.40 (3H)

8.10-7.81 (12H)

7.79-7.40 (12H)

Example 5: Compound 98

Synthesis of 4-(naphthalen-1-yl)-2-{4-(naphthalen-2-yl)phenyl}-6-{4'-(pyridin-3-yl)biphenyl-4-yl}pyrimidine The reaction was carried out under the same conditions as in Example 1 but using 2-chloro-4-(naphthalen-1-yl)-6-{4'-(pyridin-3-yl)biphenyl-4-yl}pyrimidine instead of using 2-chloro-4-phenyl-6-{4'-(pyridin-3-yl)biphenyl-4-yl}pyrimidine, and using 4-(naphthale-2-yl)phenylboronic acid instead of using 4-biphenylboronic acid.

As a result, there was obtained 1.8 g of a white powder of 4-(naphthalen-1-yl)-2-{4-(naphthalen-2-yl)phenyl}-6-{4'-(pyridin-3-yl)biphenyl-4-yl}pyrimidine (compound 98) (yield, 26%).

(Compound 98)

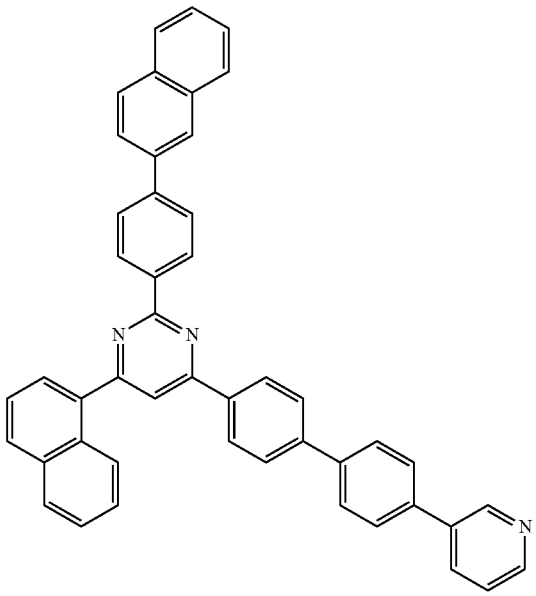

The obtained white powder was identified for its structure by the NMR. The following 31 signals of hydrogen were detected by the $^1$H-NMR (CDCl$_3$).

δ (ppm)=8.97 (1H)
8.87 (2H)
8.66 (1H)
8.50-8.40 (3H)
8.19 (1H)
8.09-7.83 (15H)
7.76 (2H)
7.69 (1H)
7.65-7.50 (4H)
7.42 (1H)

Example 6: Compound 100

Synthesis of 4-(naphthalen-2-yl)-2-{4-(naphthalen-9-yl)phenyl}-6-{4'-(pyridin-3-yl)biphenyl-4-yl}pyrimidine The reaction was carried out under the same conditions as in Example 1 but using
  2-chloro-4-(naphthalen-2-yl)-6-{4'-(pyridin-3-yl)biphenyl-4-yl}pyrimidine
instead of using
  2-chloro-4-phenyl-6-{4'-(pyridin-3-yl)biphenyl-4-yl}pyrimidine,
and using
  4-(phenanthren-9-yl)phenylboronic acid
instead of using
  4-biphenylboronic acid.
As a result, there was obtained 1.5 g of a white powder of 4-(naphthalen-2-yl)-2-{4-(phenanthren-9-yl)phenyl}-6-{4'-(pyridin-3-yl)biphenyl-4-yl}pyrimidine (compound 100) (yield, 21%).

(Compound 100)

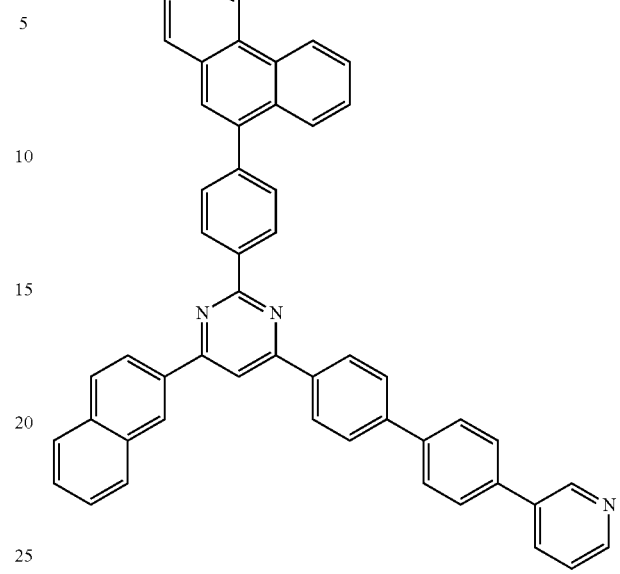

Example 7: Compound 104

Synthesis of 2-(biphenyl-3-yl)-4-(9,9-dimethylfluoren-2-yl)-6-{4'-(pyridin-3-yl)biphenyl-4-yl}pyrimidine The reaction was carried out under the same conditions as in Example 1 but using
  2-chloro-4-(9,9-dimethylfluoren-2-yl)-6-{4'-(pyridin-3-yl)biphenyl-4-yl}pyrimidine
instead of using
  2-chloro-4-phenyl-6-{4'-(pyridin-3-yl)biphenyl-4-yl}pyrimidine,
and using
  3-biphenylboronic acid
instead of using
  4-biphenylboronic acid.
As a result, there was obtained 1.8 g of a white powder of 2-(biphenyl-3-yl)-4-(9,9-dimethylfluoren-2-yl)-6-{4'-pyridin-3-yl}biphenyl-4-yl}pyrimidine (compound 104) (yield, 23%).

(Compound 104)

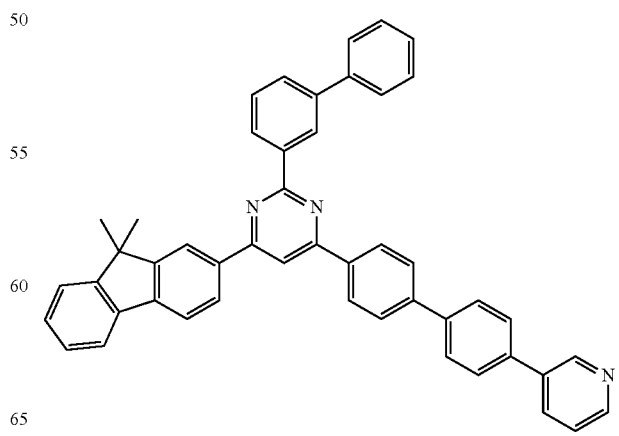

The obtained white powder was identified for its structure by the NMR. The following 35 signals of hydrogen were detected by the ¹H-NMR (CDCl₃).
δ (ppm)=9.05 (1H)
8.97 (1H)
8.78 (1H)
8.67 (1H)
8.51-8.43 (2H)
8.41-8.32 (2H)
8.17 (1H)
8.00-7.66 (13H)
7.59-7.50 (3H)
7.49-7.40 (4H)
1.67 (6H)

Example 8: Compound 107

Synthesis of 4-(biphenyl-4-yl)-2-(phenanthren-9-yl)-6-{4'-(pyridin-3-yl)biphenyl-4-yl}pyrimidine The reaction was carried out under the same conditions as in Example 1 but using
2-chloro-4-(biphenyl-4-yl)-6-{4'-(pyridin-3-yl)biphenyl-4-yl}pyrimidine
instead of using
2-chloro-4-phenyl-6-{4'-(pyridin-3-yl)biphenyl-4-yl}pyrimidine,
and using
9-phenanthreneboronic acid
instead of using
4-biphenylboronic acid.
As a result, there was obtained 2.0 g of a yellowish white powder of 4-(biphenyl-4-yl)-2-(phenanthren-9-yl)-6-{4'-pyridin-3-yl}biphenyl-4-yl}pyrimidine (compound 107) (yield, 30%).

(Compound 107)

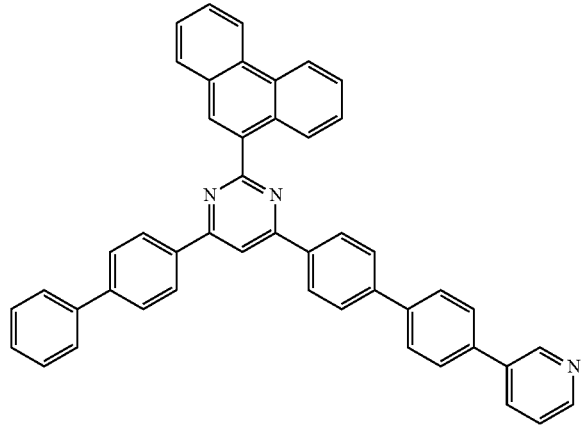

The obtained yellowish white powder was identified for its structure by the NMR. The following 31 signals of hydrogen were detected by the ¹H-NMR (CDCl₃).
δ (ppm)=8.98 (1H)
8.95-8.82 (2H)
8.80 (1H)
8.65 (1H)
8.58 (1H)
8.49-8.41 (4H)
8.29 (1H)
8.09 (1H)
7.98 (1H)
7.90-7.62 (14H)
7.52 (2H)
7.42 (2H)

<Measuring the Work Function>

By using the compounds of the invention, films were vapor-deposited in a thickness of 100 nm on an ITO substrate and were measured for their work function by using an ionization potential measuring device (Model PYS-202, manufactured by Sumitomo Heavy Industries, Ltd.).
Work Function
Compound of Example 1 (compound 1) 6.61 V
Compound of Example 2 (compound 2) 6.56 V
Compound of Example 3 (compound 29) 6.49 V
Compound of Example 4 (compound 96) 6.56 V
Compound of Example 5 (compound 98) 6.56 V
Compound of Example 6 (compound 100) 6.56 V
Compound of Example 7 (compound 104) 6.58 V
Compound of Example 8 (compound 107) 6.53 V As described above, the compounds of the present invention have values larger than a work function of 5.5 eV possessed by general hole transporting materials such as NPD, TPD and the like, and have large hole blocking powers.

<Measuring the Glass Transition Temperature>

The compounds obtained in the above Examples were measured for their glass transition temperature by using a high-sensitivity differential scanning calorimeter (DSC3100SA manufactured by Bruker AXS K.K.).
Glass Transition Temperature
Compound of Example 1 (compound 1) not measured
Compound of Example 2 (compound 2) 104° C.
Compound of Example 3 (compound 29) 137° C.
Compound of Example 4 (compound 96) 115° C.
Compound of Example 5 (compound 98) 112° C.
Compound of Example 6 (compound 100) 134° C.
Compound of Example 7 (compound 104) 110° C.
Compound of Example 8 (compound 107) 124° C.

The pyrimidine derivatives represented by the general formula (1) has glass transition temperature which is not lower than 100° C. and remain stable in their form of thin films.

Device Example 1

An organic EL device was fabricated by forming an ITO electrode as a transparent anode 2 on a glass substrate 1, and by vapor-depositing, on the ITO electrode, a hole injection layer 3, a hole transport layer 4, a luminous layer 5, a hole blocking layer 6 that also serves as an electron transport layer 7, an electron injection layer 8 and a cathode (aluminum electrode) 9 in this order.

Concretely, the glass substrate 1 having the ITO film of a thickness of 150 nm formed thereon was washed with ultrasonic waves in an isopropyl alcohol for 20 minutes and was, thereafter, dried on a hot plate heated at 200° C. for 10 minutes. Thereafter, the glass substrate with ITO was subjected to the UV-ozone treatment for 15 minutes and was placed in a vacuum vapor deposition device. The pressure therein was reduced down to 0.001 Pa or lower.

Next, the hole injection layer 3 was formed. Concretely speaking, a compound HIM-1 of the following structural formula was vapor-deposited in a thickness of 5 nm so as to cover the transparent anode 2, to thereby form the hole injection layer 3.

(HIM-1)

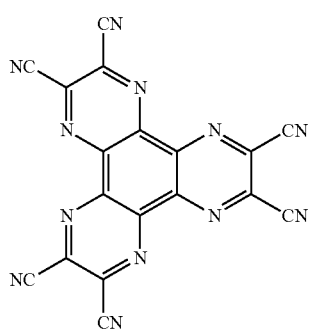

Next, the hole transport layer 4 was formed. Concretely speaking, a compound HTM-1 of the following structural formula was vapor-deposited on the hole injection layer 3 to thereby form the hole transport layer 4 in a thickness of 65 nm.

(HTM-1)

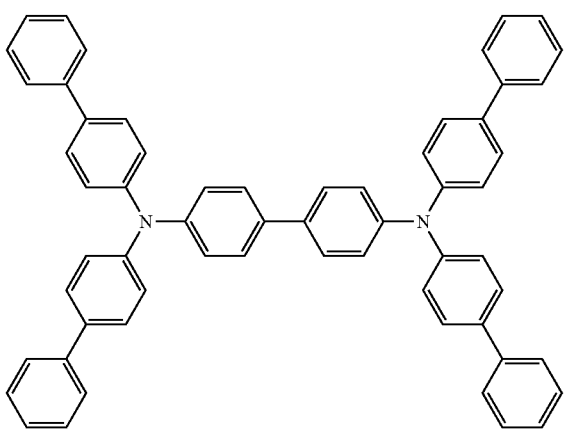

Next, the luminous layer 5 was formed. Concretely speaking, a compound EMD-1 of the following structural formula and a compound EMH-1 of the following structural formula were formed on the hole transport layer 4 by binary vapor deposition at a deposition rate of EMD-1:EMH-1=5:95 to thereby form the luminous layer 5 in a thickness of 20 nm.

(EMD-1)

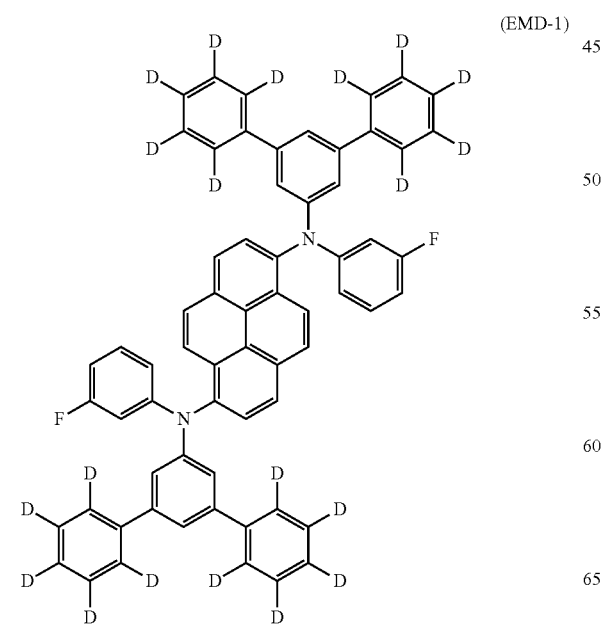

-continued (EMH-1)

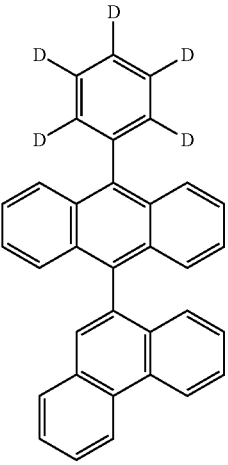

Next, the hole blocking layer 6 that also serves as the electron transport layer 7 was formed. Concretely speaking, the compound of Example 1 (compound 1) and a compound ETM-1 of the following structural formula were formed on the luminous layer 5 by binary vapor deposition at a deposition rate of compound of Example 1 (compound 1):ETM-1=50:50 to thereby form the hole blocking layer 6 that also serves as the electron transport layer 7 in a thickness of 30 nm.

(Compound 1)

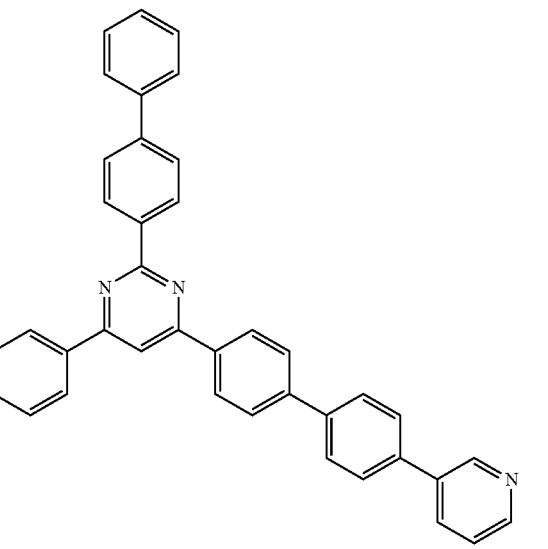

(ETM-1)

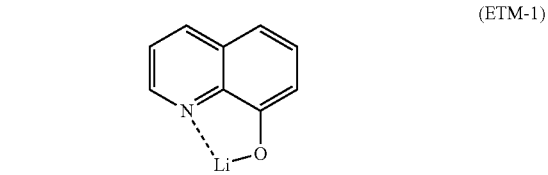

Next, the electron injection layer 8 was formed. Concretely speaking, the lithium fluoride was deposited on the hole blocking layer 6 that also serves as the electron transport layer 7 to form the electron injection layer 8 in a thickness of 1 nm.

Finally, aluminum was deposited in a thickness of 100 nm to form the cathode 9.

The EL device fabricated above was measured for its luminous characteristics when it was impressed with a direct current voltage in the atmosphere at normal temperature. The results were as shown in Table 1.

Device Example 2

An organic EL device was fabricated under the same conditions as in Device Example 1 but using, as a material for forming the hole blocking layer 6 that also serves as the electron transport layer 7, the compound of Example 2 (compound 2) instead of using the compound of Example 1 (compound 1). The EL device fabricated above was measured for its luminous characteristics when it was impressed with a direct current voltage in the atmosphere at normal temperature. The results were as shown in Table 1.

(Compound 2)

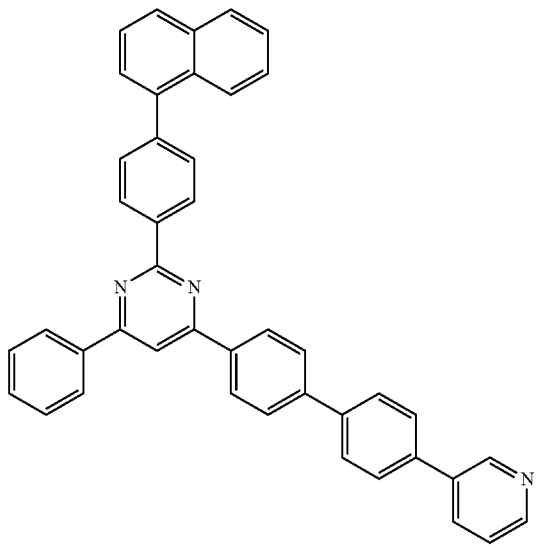

Device Example 3

An organic EL device was fabricated under the same conditions as in Device Example 1 but using, as a material for forming the hole blocking layer 6 that also serves as the electron transport layer 7, the compound of Example 3 (compound 29) instead of using the compound of Example 1 (compound 1). The EL device fabricated above was measured for its luminous characteristics when it was impressed with a direct current voltage in the atmosphere at normal temperature. The results were as shown in Table 1.

(Compound 29)

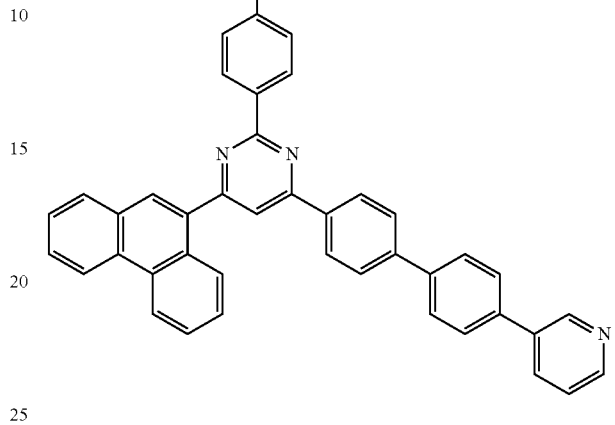

Device Example 4

An organic EL device was fabricated under the same conditions as in Device Example 1 but using, as a material for forming the hole blocking layer 6 that also serves as the electron transport layer 7, the compound of Example 4 (compound 96) instead of using the compound of Example 1 (compound 1). The EL device fabricated above was measured for its luminous characteristics when it was impressed with a direct current voltage in the atmosphere at normal temperature. The results were as shown in Table 1.

(Compound 96)

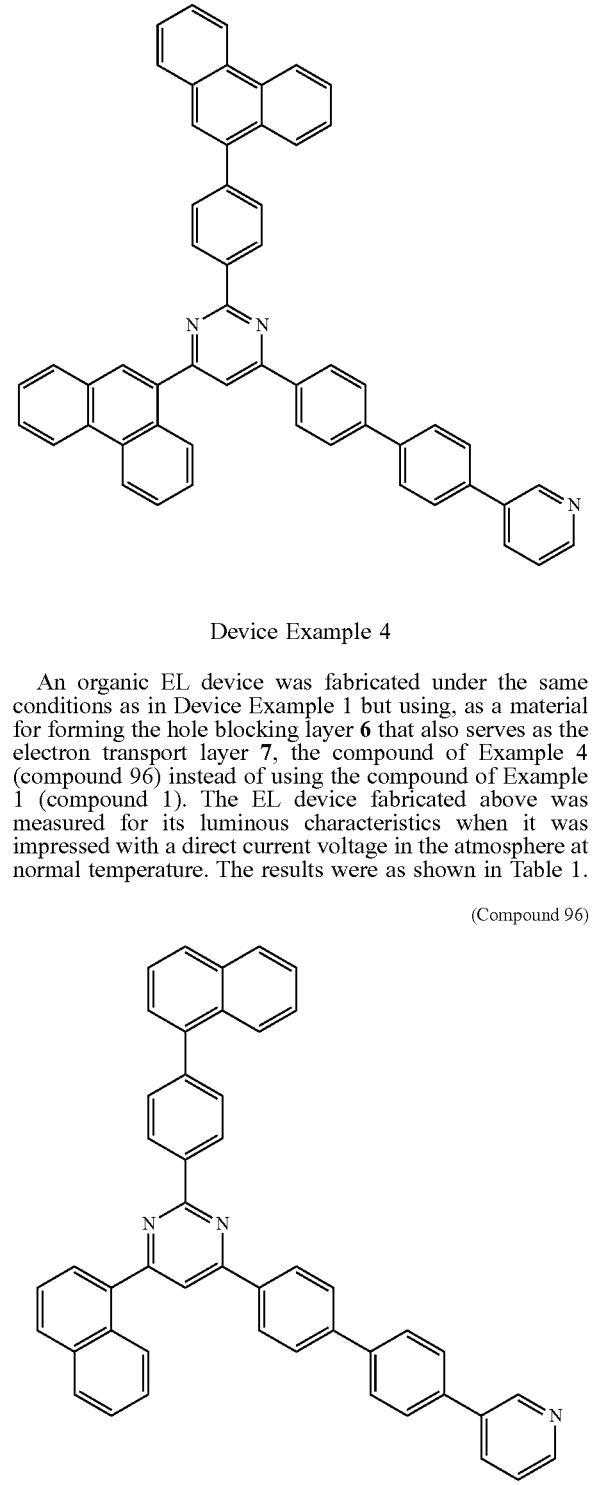

Device Example 5

An organic EL device was fabricated under the same conditions as in Device Example 1 but using, as a material for forming the hole blocking layer 6 that also serves as the electron transport layer 7, the compound of Example 5 (compound 98) instead of using the compound of Example 1 (compound 1). The EL device fabricated above was measured for its luminous characteristics when it was impressed with a direct current voltage in the atmosphere at normal temperature. The results were as shown in Table 1.

(Compound 98)

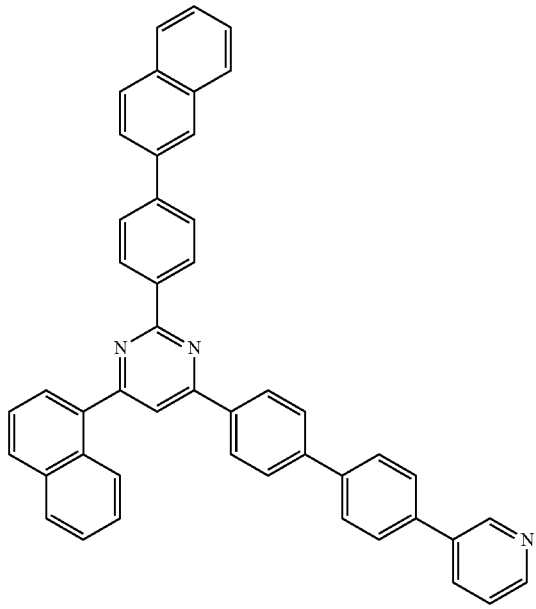

Device Example 6

An organic EL device was fabricated under the same conditions as in Device Example 1 but using, as a material for forming the hole blocking layer 6 that also serves as the electron transport layer 7, the compound of Example 6 (compound 100) instead of using the compound of Example 1 (compound 1). The EL device fabricated above was measured for its luminous characteristics when it was impressed with a direct current voltage in the atmosphere at normal temperature. The results were as shown in Table 1.

(Compound 100)

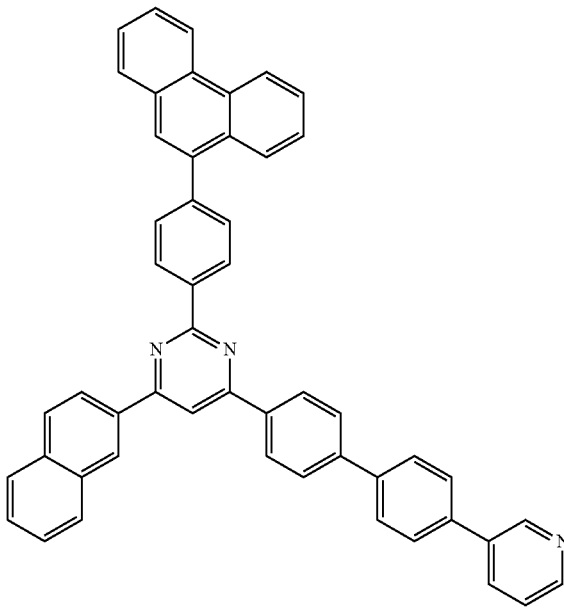

Device Example 7

An organic EL device was fabricated under the same conditions as in Device Example 1 but using, as a material for forming the hole blocking layer 6 that also serves as the electron transport layer 7, the compound of Example 7 (compound 104) instead of using the compound of Example 1 (compound 1). The EL device fabricated above was measured for its luminous characteristics when it was impressed with a direct current voltage in the atmosphere at normal temperature. The results were as shown in Table 1.

(Compound 104)

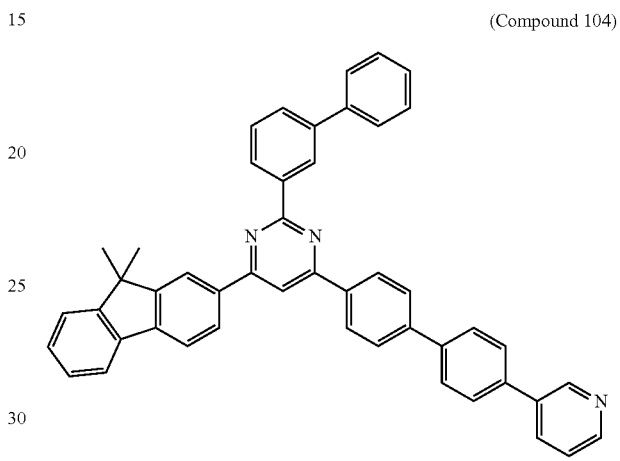

Device Example 8

An organic EL device was fabricated under the same conditions as in Device Example 1 but using, as a material for forming the hole blocking layer 6 that also serves as the electron transport layer 7, the compound of Example 8 (compound 107) instead of using the compound of Example 1 (compound 1). The EL device fabricated above was measured for its luminous characteristics when it was impressed with a direct current voltage in the atmosphere at normal temperature. The results were as shown in Table 1.

(Compound 107)

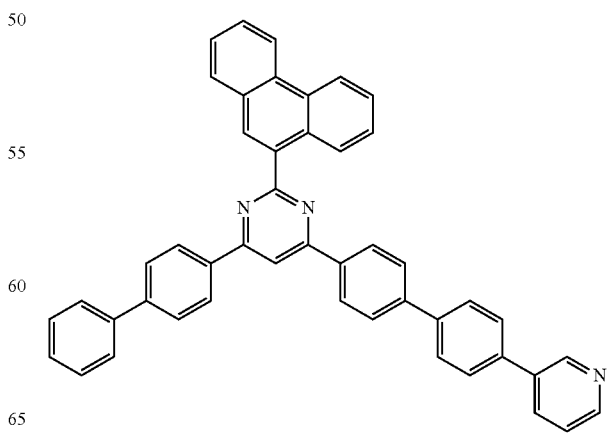

Comparative Device Example 1

An organic EL device was fabricated under the same conditions as in Device Example 1 but using, as a material for forming the hole blocking layer 6 that also serves as the electron transport layer 7, a compound ETM-2 of the following structural formula (see the patent document 2) instead of using the compound of Example 1 (compound 1). The EL device fabricated above was measured for its luminous characteristics when it was impressed with a direct current voltage in the atmosphere at normal temperature. The results were as shown in Table 1.

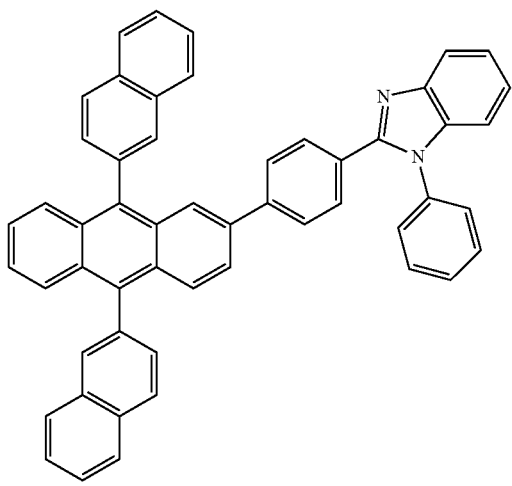

(ETM-2)

The EL device fabricated in Device Examples 1 to 8 and in Comparative Device Example 1 were measured for their device life. The results were as shown in Table 1.

The life of the devices was measured as the periods of time until when their luminance attenuated to 1900 cd/m$^2$ (corresponds to 95% when the initial luminance is 100%: 95% attenuation) from when they started emitting light at a luminance (initial luminance) of 2000 cd/m$^2$ by being driven with a constant current.

TABLE 1

| | Hole blocking/ electron transporting layer | Voltage (@10 mA/cm$^2$) [V] | Luminance (@10 mA/cm$^2$) [cd/m$^2$] | Luminous efficiency (@10 mA/cm$^2$) [cd/A] | Power efficiency (@10 mA/cm$^2$) [lm/W] | Life (till reduced down to 95%) [Hrs] |
|---|---|---|---|---|---|---|
| Device Example 1 | Compound 1/ETM-1 | 3.65 | 782 | 7.84 | 6.75 | 242 |
| Device Example 2 | Compound 2/ETM-1 | 3.74 | 795 | 7.97 | 6.71 | 241 |
| Device Example 3 | Compound 29/ETM-1 | 3.71 | 754 | 7.57 | 6.43 | 237 |
| Device Example 4 | Compound 96/ETM-1 | 3.62 | 842 | 8.43 | 7.32 | 187 |
| Device Example 5 | Compound 98/ETM-1 | 3.61 | 808 | 8.08 | 7.04 | 198 |
| Device Example 6 | Compound 100/ETM-1 | 3.76 | 714 | 7.15 | 5.98 | 262 |
| Device Example 7 | Compound 104/ETM-1 | 3.82 | 714 | 7.15 | 5.88 | 290 |
| Device Example 8 | Compound 107/ETM-1 | 3.84 | 652 | 6.53 | 5.33 | 302 |
| Comparative Device Example 1 | ETM-2/ETM-1 | 3.84 | 635 | 6.35 | 5.20 | 55 |

As shown in Table 1, the driving voltage was 3.84 V in Comparative Device Example 1 but was as low as 3.61 to 3.84 V in Device Examples 1 to 8. Further, the luminous efficiency was 6.35 cd/A in Comparative Device Example 1 but was greatly improved to be as large as 6.53 to 8.43 cd/A in Device Examples 1 to 8. The power efficiency was 5.20 lm/W in Comparative Device Example 1 which, however, was greatly improved to be 5.33 to 7.32 lm/W in Device Examples 1 to 8. Specifically, the device life was 55 hours in Comparative Example 1 but was greatly lengthened to be 187 to 302 hours in Device Examples 1 to 8.

As described above, as compared to the device that uses the compound ETM-2 that is a generally employed electron transporting material, the organic EL devices of the present invention feature excellent luminous efficiency and power efficiency and, further, provide extended device life.

INDUSTRIAL APPLICABILITY

The pyrimidine derivatives of the present invention have good electron injection property and excellent hole blocking power, remain stable in their form of thin films, and can be favorably used as compounds for fabricating the organic EL devices. Upon fabricating the organic EL devices by using the pyrimidine derivatives of the present invention, therefore, it is allowed to attain high efficiencies, to lower the driving voltages and to improve the durability. Their use can, therefore, be expanded to, for example, domestic appliances and illumination equipment.

DESCRIPTION OF REFERENCE NUMERALS 1 glass substrate
2 transparent anode
3 hole injection layer
4 hole transport layer
5 luminous layer 6 hole blocking layer
7 electron transport layer
8 electron injection layer
9 cathode

The invention claimed is:
1. Pyrimidine derivatives represented by the following formula (1-1),

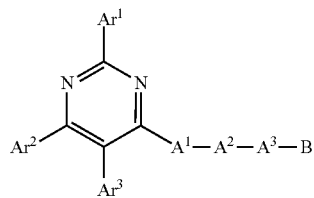

(1-1)

wherein,
Ar$^1$ is a phenyl group, a biphenylyl group, a naphthyl group, a phenanthrenyl group, a spirobifluorenyl group, a 4-(naphthyl)phenyl group, or a 4-(phenanthrenyl)phenyl group,
Ar$^2$ is a phenyl group, a biphenylyl group, a naphthyl group, a phenanthrenyl group, or a 9,9-dimethylfluorenyl group,
Ar$^3$ is a hydrogen,
both of A$^1$ and A$^2$ are phenylene groups,
A$^3$ is a single bond, and
B is a pyridyl group, a bipyridyl group, an isoquinolyl group, a naphthyridinyl group, an acridinyl group, or a phenanthrolinyl group.

2. An organic electroluminescent device having a pair of electrodes and at least one organic layer held therebetween, the at least one organic layer containing the pyrimidine derivatives of claim 1.

3. The organic electroluminescent device according to claim 2, wherein the organic layer containing the pyrimidine derivatives is an electron transport layer.

4. The organic electroluminescent device according to claim 2, wherein the organic layer containing the pyrimidine derivatives is a hole blocking layer.

5. The organic electroluminescent device according to claim 2, wherein the organic layer containing the pyrimidine derivatives is a luminous layer.

6. The organic electroluminescent device according to claim 2, wherein the organic layer containing the pyrimidine derivatives is an electron injection layer.

* * * * *